(12) United States Patent
Anvari et al.

(10) Patent No.: US 10,512,511 B2
(45) Date of Patent: Dec. 24, 2019

(54) MULTI-FUNCTION MOUNTING INTERFACE FOR AN IMAGE-GUIDED ROBOTIC SYSTEM AND QUICK RELEASE INTERVENTIONAL TOOLSET

(71) Applicant: CENTRE FOR SURGICAL INVENTION & INNOVATION, Hamilton (CA)

(72) Inventors: Mehran Anvari, Hamilton (CA); Peter D. Bevan, Toronto (CA); Steve Fisher, Schomberg (CA); Andrew P. Turner, Mississauga (CA); Tej Sachdev, Milton (CA); Timothy Scott Fielding, Mississauga (CA); Kathryn Chan, Toronto (CA)

(73) Assignee: CENTRE FOR SURGICAL INVENTION AND INNOVATION, Hamilton (CA)

( * ) Notice: Subject to any disclaimer, the term of this patent is extended or adjusted under 35 U.S.C. 154(b) by 339 days.

(21) Appl. No.: 14/906,651

(22) PCT Filed: Jul. 24, 2014

(86) PCT No.: PCT/CA2014/000591
§ 371 (c)(1),
(2) Date: Jan. 21, 2016

(87) PCT Pub. No.: WO2015/010189
PCT Pub. Date: Jan. 29, 2015

(65) Prior Publication Data
US 2016/0157941 A1    Jun. 9, 2016

Related U.S. Application Data

(60) Provisional application No. 61/857,917, filed on Jul. 24, 2013.

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/70* (2016.02); *A61B 10/0283* (2013.01); *A61B 2017/00477* (2013.01)

(58) Field of Classification Search
CPC .......... A61B 34/30; A61B 2017/00477; A61B 10/0283; A61B 10/02–06; A61B 34/70–77; A61B 1/00147–0016
(Continued)

(56) References Cited

U.S. PATENT DOCUMENTS 4,676,142 A    6/1987    McCormick et al.
4,710,079 A    12/1987    Smith et al.
(Continued)

FOREIGN PATENT DOCUMENTS

EP           0836425 B1    4/1998
WO      1994013205 A1    6/1994
(Continued)

OTHER PUBLICATIONS

PCT international Search Report and Written Opinion dated Nov. 3, 2014 re: International Application No. PCT/CA2014/000591.
(Continued)

*Primary Examiner* — Amy R Weisberg
(74) *Attorney, Agent, or Firm* — Norton Rose Fulbright Canada LLP

(57) ABSTRACT

Tool mount adaptors for interfacing a medical instrument with a medical insertion device are provided. The tool mount adaptor includes a collar for holding a medical instrument wherein the tool mount adaptor is releasably attachable to the medical insertion device. Cannula holder assemblies for
(Continued)

a medical insertion device are also provided. The cannula holder assembly includes: (a) a cannula track; and (b) a cannula carriage slideably mounted on the cannula track comprising a cannula holder mount and a demobilizer. Medical insertion devices comprising the tool mount adaptors and/or cannula holder assemblies are also provided together with methods of using the medical insertion devices in diagnostic and/or therapeutic applications.

13 Claims, 31 Drawing Sheets

(51) Int. Cl.
    *A61B 10/02* (2006.01)
    *A61B 17/00* (2006.01)

(58) Field of Classification Search
    USPC .......................................................... 606/130
    See application file for complete search history.

(56) References Cited

U.S. PATENT DOCUMENTS

| | | | |
|---|---|---|---|
| 4,791,934 A | 12/1988 | Brunnett | |
| 4,958,625 A * | 9/1990 | Bates | A61B 10/0275 600/562 |
| 5,047,015 A | 9/1991 | Foote et al. | |
| 5,078,140 A | 1/1992 | Kwoh | |
| 5,127,419 A * | 7/1992 | Kaldany | A61B 10/0275 600/567 |
| 5,176,702 A | 1/1993 | Bales et al. | |
| 5,356,421 A | 10/1994 | Castro | |
| 5,358,474 A * | 10/1994 | Kaldany | A61B 10/0275 600/567 |
| 5,427,097 A | 6/1995 | Depp | |
| 5,441,042 A | 8/1995 | Putman | |
| 5,562,613 A * | 10/1996 | Kaldany | A61B 10/0275 600/567 |
| 5,647,361 A | 7/1997 | Damadian | |
| 5,649,956 A * | 7/1997 | Jensen | B25J 9/1065 403/316 |
| 5,754,085 A | 5/1998 | Danby et al. | |
| 5,817,106 A * | 10/1998 | Real | A61B 90/11 606/130 |
| 5,820,623 A | 10/1998 | Ng | |
| 5,906,599 A * | 5/1999 | Kaldany | A61M 37/0069 604/264 |
| 6,014,070 A | 1/2000 | Danby et al. | |
| 6,023,165 A | 2/2000 | Damadian et al. | |
| 6,035,228 A | 3/2000 | Yanof et al. | |
| 6,075,364 A | 6/2000 | Damadian et al. | |
| 6,150,820 A | 11/2000 | Damadian et al. | |
| 6,165,139 A | 12/2000 | Damadian et al. | |
| 6,201,394 B1 | 3/2001 | Danby et al. | |
| 6,208,145 B1 | 3/2001 | Danby et al. | |
| 6,225,805 B1 | 5/2001 | Damadian et al. | |
| 6,249,695 B1 | 6/2001 | Damadian et al. | |
| 6,280,383 B1 | 8/2001 | Damadian | |
| 6,288,546 B1 | 9/2001 | Damadian et al. | |
| 6,298,259 B1 | 10/2001 | Kucharczyk et al. | |
| 6,335,623 B1 | 1/2002 | Damadian et al. | |
| 6,369,571 B1 | 4/2002 | Damadian et al. | |
| 6,373,251 B1 | 4/2002 | Damadian et al. | |
| 6,400,156 B1 | 6/2002 | Damadian et al. | |
| 6,404,202 B1 | 6/2002 | Damadian et al. | |
| 6,414,490 B1 | 7/2002 | Damadian et al. | |
| 6,436,107 B1 | 8/2002 | Wang et al. | |
| 6,437,571 B1 | 8/2002 | Danby et al. | |
| 6,445,185 B1 | 9/2002 | Damadian et al. | |
| 6,445,186 B1 | 9/2002 | Damadian et al. | |
| 6,451,027 B1 * | 9/2002 | Cooper | A61B 1/00149 606/130 |
| 6,456,075 B1 | 9/2002 | Damadian et al. | |
| 6,469,508 B1 | 10/2002 | Damadian et al. | |
| 6,496,007 B1 | 12/2002 | Damadian et al. | |
| 6,504,371 B1 | 1/2003 | Damadian et al. | |
| 6,505,065 B1 | 1/2003 | Yanof et al. | |
| 6,507,192 B1 | 1/2003 | Damadian et al. | |
| 6,522,145 B1 | 2/2003 | Damadian et al. | |
| 6,541,973 B1 | 4/2003 | Danby et al. | |
| 6,617,852 B1 | 9/2003 | Danby et al. | |
| 6,620,173 B2 * | 9/2003 | Gerbi | A61B 17/34 606/130 |
| 6,621,267 B1 | 9/2003 | Damadian et al. | |
| 6,785,572 B2 | 8/2004 | Yanof et al. | |
| 6,848,170 B1 | 2/2005 | Damadian et al. | |
| 6,889,073 B2 | 5/2005 | Lampman et al. | |
| 7,063,479 B2 | 6/2006 | Chinzei | |
| 7,127,802 B1 | 10/2006 | Damadian et al. | |
| 7,155,316 B2 | 12/2006 | Sutherland et al. | |
| 7,497,863 B2 * | 3/2009 | Solar | A61B 90/11 606/130 |
| 7,602,190 B2 | 10/2009 | Piferi et al. | |
| 7,666,191 B2 | 2/2010 | Orban, III et al. | |
| 7,835,780 B1 | 11/2010 | Duerk et al. | |
| 7,955,321 B2 | 6/2011 | Kishi et al. | |
| 7,955,322 B2 * | 6/2011 | Devengenzo | A61B 1/00149 606/1 |
| 7,979,108 B2 | 7/2011 | Zurn | |
| 7,979,157 B2 | 7/2011 | Anvari | |
| 8,005,571 B2 | 8/2011 | Sutherland et al. | |
| 8,041,459 B2 | 10/2011 | Sutherland et al. | |
| 8,114,032 B2 * | 2/2012 | Ferry | A61B 1/00133 600/585 |
| 8,121,361 B2 | 2/2012 | Ernst et al. | |
| 8,170,717 B2 | 5/2012 | Sutherland et al. | |
| 8,175,677 B2 | 5/2012 | Sayler et al. | |
| 8,208,993 B2 | 6/2012 | Piferi et al. | |
| 8,275,443 B2 | 9/2012 | Goldenberg et al. | |
| 8,280,485 B2 | 10/2012 | Goldenberg et al. | |
| 8,303,576 B2 | 11/2012 | Brock | |
| 8,374,411 B2 | 2/2013 | Ernst et al. | |
| 8,396,598 B2 | 3/2013 | Sutherland et al. | |
| 8,427,148 B2 | 4/2013 | O'Connor | |
| 8,503,759 B2 | 8/2013 | Greer et al. | |
| 8,571,293 B2 | 8/2013 | Greer et al. | |
| 8,670,816 B2 | 3/2014 | Green et al. | |
| 8,781,630 B2 | 7/2014 | Banks et al. | |
| 8,812,077 B2 | 8/2014 | Dempsey | |
| 8,886,287 B2 | 11/2014 | Larson et al. | |
| 8,909,319 B2 | 12/2014 | Larson et al. | |
| 8,979,871 B2 | 3/2015 | Tye et al. | |
| 8,986,246 B2 | 3/2015 | Foley et al. | |
| 9,049,988 B2 | 6/2015 | Zurn | |
| 9,076,212 B2 | 7/2015 | Ernst et al. | |
| 9,097,756 B2 | 8/2015 | Piferi | |
| 9,138,175 B2 | 9/2015 | Ernst et al. | |
| 9,211,157 B2 | 12/2015 | Tye et al. | |
| 9,220,567 B2 | 12/2015 | Sutherland et al. | |
| 9,222,996 B2 | 12/2015 | Fujimoto et al. | |
| 9,259,195 B2 | 2/2016 | Yanof et al. | |
| 9,259,271 B2 * | 2/2016 | Anvari | A61B 10/0266 |
| 9,271,664 B2 | 3/2016 | Wedan et al. | |
| 9,326,823 B2 | 5/2016 | McMillan et al. | |
| 9,326,825 B2 | 5/2016 | Cleary et al. | |
| 9,492,241 B2 | 11/2016 | Joskowicz et al. | |
| 9,504,484 B2 | 11/2016 | Andrew et al. | |
| 9,510,909 B2 | 12/2016 | Grant et al. | |
| 9,538,991 B2 | 1/2017 | Menon et al. | |
| 9,539,058 B2 | 1/2017 | Tsekos et al. | |
| 9,554,779 B2 | 1/2017 | Larson et al. | |
| 9,561,083 B2 | 2/2017 | Yu et al. | |
| 9,575,148 B2 | 2/2017 | Winter et al. | |
| 9,603,672 B2 * | 3/2017 | Shellenberger | A61B 34/30 |
| 9,700,342 B2 | 7/2017 | Andrews et al. | |
| 9,737,371 B2 | 8/2017 | Romo et al. | |
| 9,763,741 B2 | 9/2017 | Alvarez et al. | |
| 9,844,412 B2 | 12/2017 | Bogusky et al. | |
| 9,844,414 B2 | 12/2017 | Fischer et al. | |
| 9,855,103 B2 | 1/2018 | Tsekos et al. | |
| 9,867,549 B2 | 1/2018 | Ernst et al. | |
| 9,877,788 B2 | 1/2018 | Stoianovici et al. | |

(56) References Cited

U.S. PATENT DOCUMENTS

| | | | |
|---|---|---|---|
| 9,974,619 B2 | 5/2018 | Goldenberg et al. | |
| 9,987,096 B2 | 6/2018 | Larson et al. | |
| 9,993,302 B2 | 6/2018 | Zurn | |
| 10,010,308 B2 | 7/2018 | Zhou et al. | |
| 10,022,192 B1 | 7/2018 | Ummalaneni | |
| 10,117,632 B2 | 7/2018 | Johnson et al. | |
| 10,143,526 B2 | 12/2018 | Walker et al. | |
| 2002/0120252 A1* | 8/2002 | Brock | A61B 17/0469 606/1 |
| 2002/0156395 A1* | 10/2002 | Stephens | A61B 10/0275 600/567 |
| 2004/0193146 A1* | 9/2004 | Lee | A61B 17/062 606/1 |
| 2005/0165328 A1* | 7/2005 | Heske | A61B 10/0275 600/566 |
| 2006/0074344 A1* | 4/2006 | Hibner | A61B 10/0275 600/566 |
| 2006/0074346 A1* | 4/2006 | Hibner | A61B 10/0275 600/566 |
| 2006/0122496 A1 | 6/2006 | George et al. | |
| 2006/0149163 A1* | 7/2006 | Hibner | A61B 10/0266 600/566 |
| 2007/0119274 A1* | 5/2007 | Devengenzo | B25J 15/04 74/490.01 |
| 2007/0219443 A1 | 9/2007 | Ehnholm et al. | |
| 2007/0239067 A1* | 10/2007 | Hibner | A61B 10/0041 600/567 |
| 2008/0140088 A1* | 6/2008 | Orban, III | A61B 34/30 606/130 |
| 2008/0167674 A1* | 7/2008 | Bodduluri | A61M 5/20 606/187 |
| 2008/0249536 A1* | 10/2008 | Stahler | A61B 34/71 606/130 |
| 2009/0024141 A1* | 1/2009 | Stahler | A61B 34/71 606/130 |
| 2009/0088666 A1* | 4/2009 | Miller | A61B 10/0275 600/568 |
| 2010/0030233 A1* | 2/2010 | Whitman | A61B 34/30 606/130 |
| 2010/0036245 A1* | 2/2010 | Yu | A61N 5/1027 600/439 |
| 2010/0041938 A1 | 2/2010 | Stoianovici et al. | |
| 2010/0160810 A1* | 6/2010 | Parihar | A61B 90/11 600/562 |
| 2010/0280525 A1* | 11/2010 | Alvarez | A61B 17/00234 606/130 |
| 2011/0098553 A1 | 4/2011 | Robbins et al. | |
| 2012/0150019 A1 | 6/2012 | Elgort et al. | |
| 2012/0190965 A1 | 7/2012 | Schaerer et al. | |
| 2012/0190966 A1 | 7/2012 | Schaerer et al. | |
| 2012/0265051 A1 | 10/2012 | Fischer et al. | |
| 2012/0310112 A1 | 12/2012 | Fichtinger et al. | |
| 2013/0035583 A1 | 2/2013 | Park et al. | |
| 2013/0072784 A1 | 3/2013 | Velusamy | |
| 2013/0085380 A1 | 4/2013 | Velusamy | |
| 2013/0218005 A1 | 8/2013 | Desai et al. | |
| 2013/0231586 A1 | 9/2013 | Tsonton et al. | |
| 2013/0282021 A1* | 10/2013 | Parihar | A61B 17/105 606/130 |
| 2013/0296883 A1 | 11/2013 | Anvari | |
| 2013/0296886 A1 | 11/2013 | Green et al. | |
| 2014/0107665 A1* | 4/2014 | Shellenberger | A61B 34/30 606/130 |
| 2014/0180074 A1 | 6/2014 | Green et al. | |
| 2014/0309661 A1* | 10/2014 | Sheps | A61M 25/0147 606/130 |
| 2014/0330108 A1 | 11/2014 | Dempsey | |
| 2015/0066428 A1 | 3/2015 | Larson et al. | |
| 2015/0073433 A1 | 3/2015 | Schaerer et al. | |
| 2015/0087961 A1 | 3/2015 | Tyc et al. | |
| 2015/0087962 A1 | 3/2015 | Tyc et al. | |
| 2015/0100067 A1 | 4/2015 | Cavanagh et al. | |
| 2015/0119638 A1 | 4/2015 | Yu et al. | |
| 2015/0150637 A1 | 6/2015 | Iwasa | |
| 2015/0164594 A1 | 6/2015 | Romo et al. | |
| 2015/0164596 A1 | 6/2015 | Romo | |
| 2015/0257841 A1* | 9/2015 | Dachs, II | A61B 90/361 606/130 |
| 2015/0265353 A1 | 9/2015 | Andrews et al. | |
| 2015/0335316 A1 | 11/2015 | Darrow et al. | |
| 2015/0366624 A1 | 12/2015 | Kostrzewski et al. | |
| 2016/0001038 A1 | 1/2016 | Romo et al. | |
| 2016/0270865 A1 | 9/2016 | Landey et al. | |
| 2016/0302871 A1 | 10/2016 | Gregerson et al. | |
| 2017/0014203 A1 | 1/2017 | Mathelin et al. | |
| 2017/0086927 A1* | 3/2017 | Auld | A61B 34/30 |
| 2017/0086932 A1* | 3/2017 | Auld | A61B 34/71 |
| 2017/0100195 A1 | 4/2017 | Velusamy | |
| 2017/0100199 A1 | 4/2017 | Yu et al. | |
| 2017/0112410 A1 | 4/2017 | Menon et al. | |
| 2017/0165019 A1* | 6/2017 | Penny | A61B 34/71 |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |
| 2017/0296289 A1 | 10/2017 | Andrews et al. | |
| 2017/0311880 A1 | 11/2017 | Jacobsen et al. | |
| 2017/0340396 A1 | 11/2017 | Romo et al. | |
| 2017/0367776 A1 | 12/2017 | Kwok et al. | |
| 2017/0371001 A1 | 12/2017 | Dempsey | |
| 2018/0049826 A1 | 2/2018 | Fischer et al. | |
| 2018/0116741 A1* | 5/2018 | Garcia Kilroy | G01L 3/1428 |
| 2018/0116759 A1 | 5/2018 | Chen et al. | |
| 2018/0132954 A1 | 5/2018 | Nazim et al. | |
| 2018/0185113 A1 | 7/2018 | Gregerson et al. | |
| 2018/0207794 A1 | 7/2018 | Sebring et al. | |
| 2018/0249927 A1 | 9/2018 | Ernst et al. | |
| 2018/0280223 A1 | 10/2018 | Hiratsuka et al. | |
| 2018/0289344 A1 | 10/2018 | Green et al. | |
| 2018/0289575 A1 | 10/2018 | Hiratsuka et al. | |
| 2018/0296121 A1 | 10/2018 | Coppens et al. | |
| 2018/0296406 A1 | 10/2018 | Coppens et al. | |

FOREIGN PATENT DOCUMENTS

| | | |
|---|---|---|
| WO | 1996008199 A1 | 3/1996 |
| WO | 9639944 | 12/1996 |
| WO | 2000023000 A1 | 4/2000 |
| WO | 2001075465 A1 | 10/2001 |
| WO | 2003045264 A1 | 6/2003 |
| WO | 2004014244 A2 | 2/2004 |
| WO | 2004069492 A2 | 8/2004 |
| WO | 2004110242 A2 | 12/2004 |
| WO | 2006025001 A1 | 3/2006 |
| WO | 2007136745 A2 | 11/2007 |
| WO | 2008153975 A2 | 12/2008 |
| WO | 2009040677 A2 | 4/2009 |
| WO | 2009042130 A2 | 4/2009 |
| WO | 2009042131 A1 | 4/2009 |
| WO | 2009042135 A2 | 4/2009 |
| WO | 2009042136 A1 | 4/2009 |
| WO | 2009042152 A1 | 4/2009 |
| WO | 2009042155 A2 | 4/2009 |
| WO | 2009042160 A1 | 4/2009 |
| WO | 2009146176 A1 | 12/2009 |
| WO | 2009152613 A1 | 12/2009 |
| WO | 2010034099 A1 | 4/2010 |
| WO | 2010044852 A3 | 4/2010 |
| WO | 2011050456 A1 | 5/2011 |
| WO | 2011057260 A2 | 5/2011 |
| WO | 2011063511 A1 | 6/2011 |
| WO | 2012063266 A3 | 5/2012 |
| WO | 2012088321 A1 | 6/2012 |
| WO | 2013041994 A2 | 3/2013 |
| WO | 2013116240 A1 | 8/2013 |
| WO | 2013187342 A2 | 12/2013 |
| WO | 2014003855 A1 | 1/2014 |
| WO | 2014032046 A1 | 2/2014 |
| WO | 2014036034 A1 | 3/2014 |
| WO | 2014058833 A1 | 4/2014 |
| WO | 2014204930 A3 | 12/2014 |
| WO | 2015061756 A1 | 4/2015 |
| WO | 2015124795 A1 | 8/2015 |

(56) References Cited

FOREIGN PATENT DOCUMENTS

| | | |
|---|---|---|
| WO | 2015143026 A1 | 9/2015 |
| WO | 2015193479 A1 | 12/2015 |
| WO | 2016054256 A1 | 4/2016 |
| WO | 2016149125 A1 | 9/2016 |
| WO | 2016168671 A1 | 10/2016 |
| WO | 2016176683 A1 | 11/2016 |
| WO | 2017066616 A1 | 4/2017 |
| WO | 2017066628 A3 | 4/2017 |
| WO | 2017098543 A1 | 6/2017 |
| WO | 2017098544 A1 | 6/2017 |
| WO | 2017099234 A1 | 6/2017 |
| WO | 2017136550 A1 | 8/2017 |
| WO | 2017158180 A1 | 9/2017 |
| WO | 2017189874 A1 | 11/2017 |
| WO | 2017220010 A1 | 12/2017 |
| WO | 2017223382 A1 | 12/2017 |
| WO | 2018049196 A1 | 3/2018 |
| WO | 2018053282 A1 | 3/2018 |
| WO | 2018081136 A3 | 5/2018 |

OTHER PUBLICATIONS

English language translation of WO2004/069492 dated Aug. 19, 2004.

English translations of International Patent Application No. WO 2017/098543 dated Jun. 15, 2017, https://patents.google.com/patent/JPWO2017098543A1/en?oq=WO2017098543, accessed on Jul. 19, 2019.

English translations of International Patent Application No. WO 2017/098544 dated Jun. 15, 2017, https://patents.google.com/patent/WO2017098544A1/en?oq=WO2017098544, accessed on Jul. 19, 2019.

English translations of International Patent Application No. WO 2017/099234 dated Jun. 15, 2017, https://patents.google.com/patent/WO2017099234A1/en?oq=WO2017099234A1, accessed on Jul. 19, 2019.

* cited by examiner

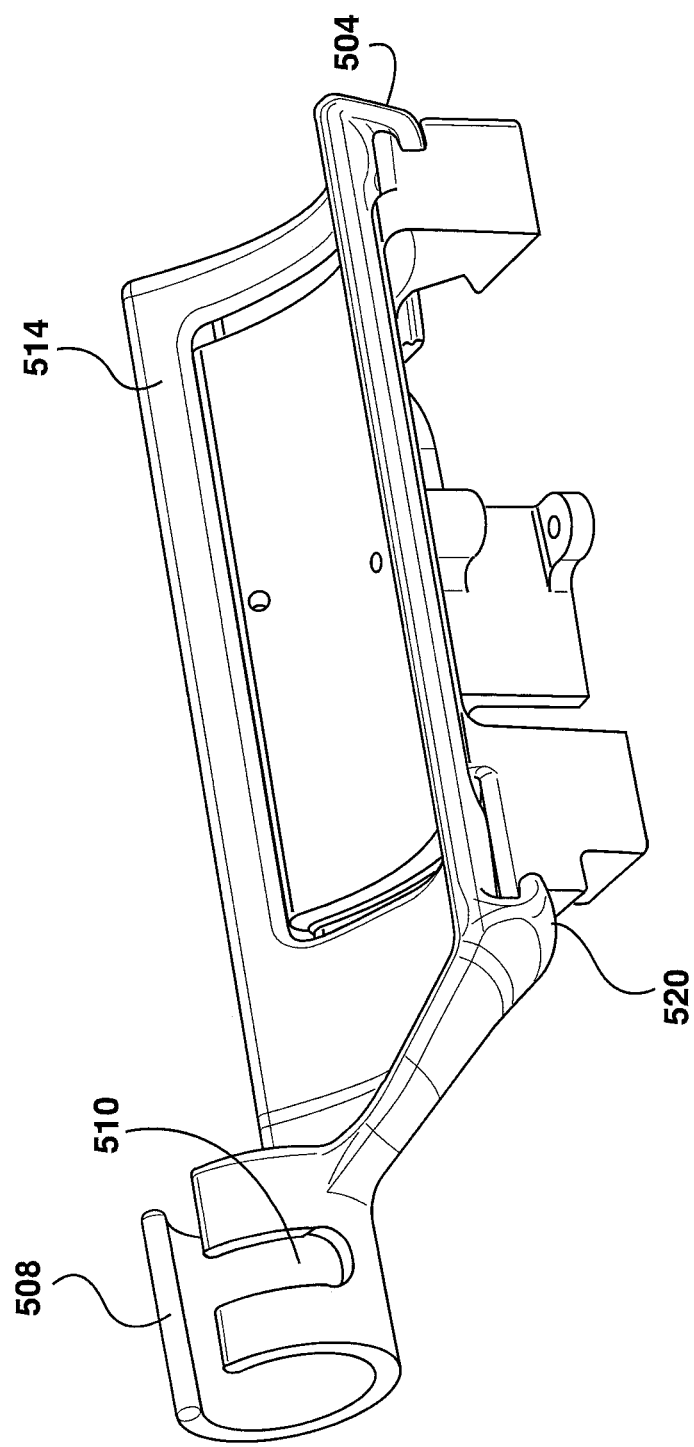

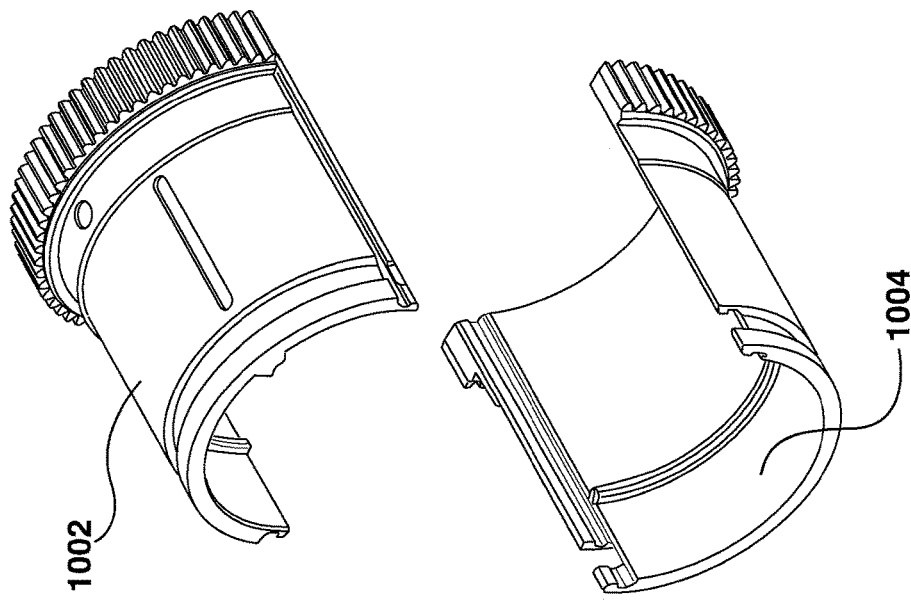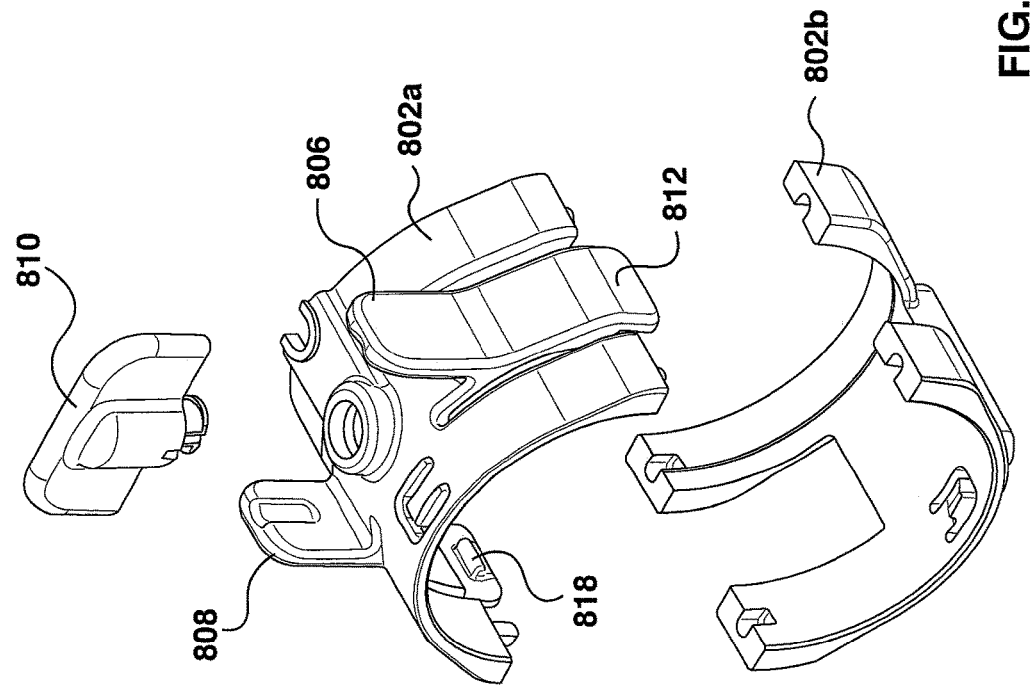
FIG. 25

MULTI-FUNCTION MOUNTING INTERFACE FOR AN IMAGE-GUIDED ROBOTIC SYSTEM AND QUICK RELEASE INTERVENTIONAL TOOLSET

CROSS REFERENCE TO RELATED APPLICATIONS

This application is a national phase application under 35 U.S.C. 371 of International Patent Application No. PCT/CA2014/000591 filed on Jul. 24, 2014, which claims the benefit of U.S. Provisional Patent Application Ser. No. 61/857,917 entitled "MULTI-FUNCTION MOUNTING INTERFACE FOR AN IMAGE-GUIDED ROBOTIC SYSTEM AND QUICK RELEASE INTERVENTIONAL TOOLSET" filed on Jul. 24, 2013, which is incorporated herein by reference in its entirety.

FIELD OF INVENTION

This invention relates to surgical robotics, and in particular the control of medical instruments which have an insertion action, such as a biopsy needle or ablation tool.

BACKGROUND

Cancer diagnosis and treatment can require the medical practitioner to be able to pin point a suspicious lesion within the patient. After the area is located, the next step in a typical treatment process can include a biopsy procedure to identify the pathology, which can be performed in the operating room, with the patient under general anesthetic. In other instances, biopsy procedures can include the implementation of core needle biopsy procedures using minimally invasive core needle extraction methods.

Difficulties can arise in performing a conventional procedure. As an example, for breast biopsy with magnetic resonance imaging (MRI) systems, the patient may have to be shuttled in and out of the magnet several times before a biopsy is actually performed. During this time, the contrast agent could have already lost some of its effect and image quality could suffer. This process itself may be time consuming and cumbersome, especially in a time-sensitive environment.

In addition, contrast laden blood from a hematoma as well as an air pocket at the biopsy site can make it difficult to subsequently verify that the correct site identified from the imaging system was biopsied, or to rapidly confirm that the sample obtained has a suspect morphology. This practice could also require removal of a relatively large volume of tissue, with a fraction of that assumed to be from the lesion.

In order to retrieve tissue for diagnosis or treatment, medical technology has advanced to the point that medical instruments can be inserted into a body toward a suspected lesion. The insertion procedure can be made more useful if it is adapted to accommodate a variety of medical instruments in a safe and minimally invasive manner.

SUMMARY

According to an embodiment, there is provided a tool mount adaptor for interfacing a medical instrument with a medical insertion device, the tool mount adaptor comprising a collar for holding a medical instrument, wherein the tool mount adaptor is releasably attachable to the medical insertion device. In some embodiments, the collar comprises a first piece and a second piece, wherein the first piece and the second piece are releasably connectable to form the collar. In other embodiments, a first end of the first piece is releasably connectable with a first end of the second piece and a second end of the first piece is releasably connectable with a second end of the second piece to form the collar. In further embodiments, the tool mount adaptor further comprises a locking mechanism, wherein the locking mechanism is adapted to restrict separation of the first piece and the second piece when in a locked mode and allow separation of the first piece and the second piece when in an unlocked mode. In other embodiments, the tool mount adaptor further comprises a locking mechanism, wherein: when in a locked mode, the locking mechanism restricts separation of the first piece and the second piece and restricts detachment of the tool mount adaptor from the medical insertion device; and when in an unlocked mode, the locking mechanism allows separation of the first piece and the second piece and allows detachment of the tool mount adaptor from the medical insertion device. In other embodiments, the tool mount adaptor is attached to the medical insertion device by way of an end effector interface and the tool mount adaptor further comprises a locking mechanism, wherein: when in a locked mode, the locking mechanism restricts separation of the first piece and the second piece and restricts detachment of the tool mount adaptor from the end effector interface; and when in an unlocked mode, the locking mechanism allows separation of the first piece and the second piece and allows detachment of the tool mount adaptor from the end effector interface. In other embodiments of the tool mount adaptor, the medical insertion device comprises lateral receiving members and the collar comprises engaging members adapted to engage the receiving members. In further embodiments of the tool mount adaptor, the receiving members define apertures and the engaging members comprise a nub complementary to the apertures. In other embodiments, the tool mount adaptor is attached to the medical insertion device by way of an end effector interface and the end effector interface comprises lateral receiving members and the collar comprises engaging members adapted to engage the receiving members. In further embodiments of the tool mount adaptor, the receiving members define apertures and the engaging members comprise a nub complementary to the apertures. In some embodiments, the tool mount adaptor may further comprise a latch to secure the medical instrument to the collar. In other embodiments, the tool mount adaptor further comprises a tool interface feature formed along an interior surface of the collar, wherein the tool interface feature is adapted to fit an outer surface of the medical instrument held in the collar. In other embodiments, the tool mount adaptor further comprises a tool interface feature placed along an interior surface of the collar, wherein the tool interface feature is adapted to fit an outer surface of the medical instrument held in the collar. In other embodiments, the tool mount adaptor further comprises a demobilizer-disengaging member. In alternative embodiments, the tool mount adaptor is adapted to attach to the medical insertion device lateral to an axis of insertion direction of the medical instrument.

According to another embodiment, there is provided a cannula holder assembly for a medical insertion device comprising: (a) a cannula track; and (b) a cannula carriage slideably mounted on the cannula track comprising a cannula holder mount and a demobilizer, wherein the demobilizer in a demobilization mode is adapted to restrict movement of the cannula carriage along the cannula track and in a mobilization mode allows movement of the cannula carriage along the cannula track. In other embodiments, the cannula track comprises a first set of teeth and the demobilizer comprises a first pawl adapted to engage the first set of teeth. In further embodiments, the demobilizer comprises a first lever adapted to disengage the first pawl. In some embodiments, the cannula track comprises a second set of teeth and the demobilizer comprises a second pawl adapted to engage the second set of teeth. In alternative embodiments, the demobilizer comprises a second lever adapted to disengage the second pawl. In further embodiments, the cannula holder assembly further comprises a toggle for disengaging the first pawl when the second pawl is disengaged, and the second pawl when the first pawl is disengaged. In other embodiments, the cannula carriage further comprises a cannula holder for receiving a cannula, the cannula holder being releasably attachable to the cannula holder mount.

According to a further embodiment, there is provided a medical insertion device comprising: (a) a frame; and (b) a carriage assembly connected to the frame comprising: (i) a mounting arm comprising an insertion track; (ii) an insertion carriage adapted to move along the insertion track; and (iii) a tool mount adaptor connected to the insertion carriage, the tool mount adaptor comprising a collar for a medical instrument, wherein the tool mount adaptor is releasably attachable to the insertion carriage. In other embodiments, the medical insertion device further comprises a linear slide assembly connected to the frame, wherein the carriage assembly is connected to the frame by way of the linear slide assembly, and the carriage assembly is adapted to move along the linear slide assembly. In some embodiments, the medical insertion device further comprises a rotary drive assembly for driving the linear drive assembly. In alternative embodiments, the insertion carriage comprises a motor to propel the insertion carriage along the insertion track. In some embodiments, the mounting arm of the carriage assembly further comprises a cannula track parallel to the insertion track; the carriage assembly further comprises a cannula carriage, the cannula carriage comprising a demobilizer and a cannula holder mount for receiving a cannula, and the cannula carriage is adapted to move along the cannula track; and the demobilizer in a demobilization mode is adapted to restrict movement of the cannula carriage along the cannula track and in a mobilization mode allows movement of the cannula carriage along the cannula track. In other embodiments, the insertion carriage includes a demobilizer-disengaging member adapted to set the demobilizer to a mobilization mode. In further embodiments, the medical instrument connected to the insertion carriage is adapted to work cooperatively with the cannula connected to the cannula carriage. In other embodiments, the medical insertion device interfaces with the tool mount adaptor so that an off-the-shelf tool or a custom tool is aligned with a known trajectory. In further embodiments, the medical insertion device interfaces with the tool mount adaptor to actuate at least one functionality of the medical instrument. In some embodiments, the at least one functionality is a trocar functionality, a syringe functionality, a needle functionality, a fibreoptic sensing functionality, an interstitial imaging device functionality, a biopsy tool functionality, a probing functionality or an ablative tool functionality. In some embodiments, the at least one functionality is a tool rolling functionality. In other embodiments, the at least one functionality is an injection functionality.

According to another embodiment, there is provided a method for facilitating insertion of a medical instrument in a patient using a medical insertion device, the medical insertion device comprising: (a) a frame; and (b) a carriage assembly connected to the frame comprising: (i) a mounting arm comprising: (1) an insertion track; and (2) a cannula track parallel to the insertion track; (ii) an insertion carriage adapted to move along the insertion track; and (iii) a tool mount adaptor connected to the insertion carriage, the tool mount adaptor comprising a collar for holding a medical instrument, wherein the tool mount adaptor is releasably attachable to the insertion carriage; and (iv) a cannula carriage adapted to move along the cannula track, the cannula carriage comprising: (1) a demobilizer, wherein the demobilizer in a demobilization mode is adapted to restrict movement of the cannula carriage along the cannula track and in a mobilization mode allows movement of the cannula carriage along the cannula track; and (2) a cannula holder mount for receiving a cannula, the method comprising: (A) securing a medical instrument in the collar of the tool mount adaptor and moving the insertion carriage along the insertion track in an insertion direction to insert the medical instrument into the patient; or (B) moving the insertion carriage along the insertion track in a direction opposite to the insertion direction to retract the medical instrument from the patient and optionally removing the medical instrument from the collar; or (C) securing a medical instrument in the collar of the tool mount adaptor, moving the insertion carriage along the insertion track in an insertion direction to insert the medical instrument into the patient, actuating at least one functionality of the medical instrument held within the tool mount adaptor, moving the insertion carriage along the insertion track in a direction opposite to the insertion direction to retract the medical instrument from the patient and optionally removing the medical instrument from the collar; or (D) securing a cannula to the cannula holder mount and moving the cannula carriage along the cannula track in the insertion direction to insert the cannula into the patient; or (E) moving the cannula carriage along the cannula track in a direction opposite to the insertion direction to retract the cannula from the patient and optionally removing the cannula from the cannula holder mount; or (F) securing a cannula to the cannula holder mount, moving the cannula carriage along the cannula track in the insertion direction to insert the cannula into the patient, moving the cannula carriage along the cannula track in a direction opposite to the insertion direction to retract the cannula from the patient and optionally removing the cannula from the cannula holder mount; (G) actuating at least one functionality of the medical instrument held within the tool mount adaptor; or (H) any combination of steps A, B, C, D, E, F and G, or any combination of any subset of steps A, B, C, D, E, F and G, performed in any order where any one of steps A, B, C, D, E, F and G is performed one or more times. In other embodiments, any one of steps A, B, C, D, E, F and G is performed one time, two times, three times, four times, five times, six times, seven times, eight times, nine times or ten times. In further embodiments, any one of steps A, B, C and G is performed one or more times wherein the medical instrument is any one of a trocar, a syringe, a needle, a fibreoptic sensor, an interstitial imaging device, a biopsy tool, a probe and an ablative tool. In other embodiments, the same or a different medical instrument can be used for each of steps A, B, C and G. In further embodiments, the same or a different medical instrument can be used for each step A, for each step B, for each step C and for each step G when any one of steps A, B, C and G is performed two or more times. In some embodiments, the method comprises step C wherein the medical instrument is a trocar, a syringe, a needle, a fibreoptic sensor, an interstitial imaging device, a biopsy tool, a probe or an ablative tool and the medical instrument is removed from the collar after retracting the medical instrument from the patient. In further embodiments, the method comprises step C wherein the at least one functionality is a trocar functionality, a syringe functionality, a needle functionality, a fibreoptic sensing functionality, an interstitial imaging device functionality, a biopsy tool functionality, a probing functionality or an ablative tool functionality. In some embodiments, the method comprises step G wherein the at least one functionality is a trocar functionality, a syringe functionality, a needle functionality, a fibreoptic sensing functionality, an interstitial imaging device functionality, a biopsy tool functionality, a probing functionality or an ablative tool functionality. In some embodiments, the at least one functionality is a tool rolling functionality. In other embodiments, the at least one functionality is an injection functionality. In other embodiments, the method comprises step F wherein the cannula is removed from the cannula holder mount after retracting the cannula from the patient. In some embodiments, the method comprises securing an anesthesia tool in the collar, moving the insertion carriage along the insertion track in an insertion direction to insert the anesthesia tool into the patient, moving the insertion carriage along the insertion track in a direction opposite to the insertion direction to retract the anesthesia tool from the patient and removing the anesthesia tool from the collar; securing a trocar in the collar and moving the insertion carriage along the insertion track in an insertion direction to insert the trocar into a single access point of a patient; securing a cannula to the cannula holder mount and moving the cannula carriage along the cannula track in the insertion direction to insert the cannula into the single access point of the patient; moving the insertion carriage along the insertion track in a direction opposite to the insertion direction to retract the trocar from the patient and removing the trocar from the collar; securing a vacuum assisted biopsy tool to the collar and moving the insertion carriage along the insertion track in the insertion direction to insert the vacuum assisted biopsy tool into the single access point of the patient and through a hollow body of the cannula; moving the insertion carriage along the insertion track in a direction opposite to the insertion direction to retract the vacuum assisted biopsy tool from the patient and removing the vacuum assisted biopsy tool from the collar; and moving the cannula carriage along the cannula track in a direction opposite to the insertion direction to retract the cannula from the patient and removing the cannula from the cannula holder mount.

In some embodiments, the medical instrument is a needle-based diagnostic or therapeutic device. In other embodiments, the medical instrument is a trocar, a syringe, a needle, a fibreoptic sensor, an interstitial imaging device, a biopsy tool, a probe, an ablative tool or a cannula. In other embodiments, the medical instrument is a trocar, a syringe, a needle, a fibreoptic sensor, an interstitial imaging device, a biopsy tool, a probe or an ablative tool. In some embodiments, the medical instrument is a trocar, a syringe, or a biopsy instrument. In some embodiments, the medical instrument is a cutting tool. For example, the medical instrument is a trocar. In further embodiments, the medical instrument is an anesthesia tool. For example, the medical instrument is a syringe. In other embodiments, the medical instrument is an off-the-shelf syringe. In further embodiments, the medical instrument is a biopsy tool. For example, the medical instrument is a vacuum assisted biopsy tool. In other embodiments, the medical instrument is an off-the-shelf biopsy tool. In another embodiment, the medical instrument is an ablative tool. For example, the medical instrument is a radiofrequency ablation tool, a focused ultrasound instrument, a cryotherapy tool or a laser. In some embodiments, the medical instrument is a detector. For example, the medical instrument is a probe or an MRI coil. In other embodiments, the medical instrument is an ultrasound probe or a fiber optic probe. In some embodiments, the medical instrument is an MRI coil. In some embodiments, the medical instrument may include one or more end effectors.

BRIEF DESCRIPTION OF THE DRAWINGS

Embodiments of the invention are illustrated in the figures of the accompanying drawings, which are meant to be exemplary and not limiting.

FIG. 11 is a perspective view showing a cannula holder coupled to a cannula holder mount according to various embodiments of the invention.

FIG. 25 is an exploded view of the tool mount adaptor shown in FIG. 23.

DETAILED DESCRIPTION

For a more complete understanding of the present invention, reference is now made to the following description and accompanying drawings, which individually and together illustrate embodiments in which the invention may be practiced. These embodiments may be combined and elements may be changed, as would be obvious to persons skilled in the art, without departing from the scope of the invention.

Figure 1:
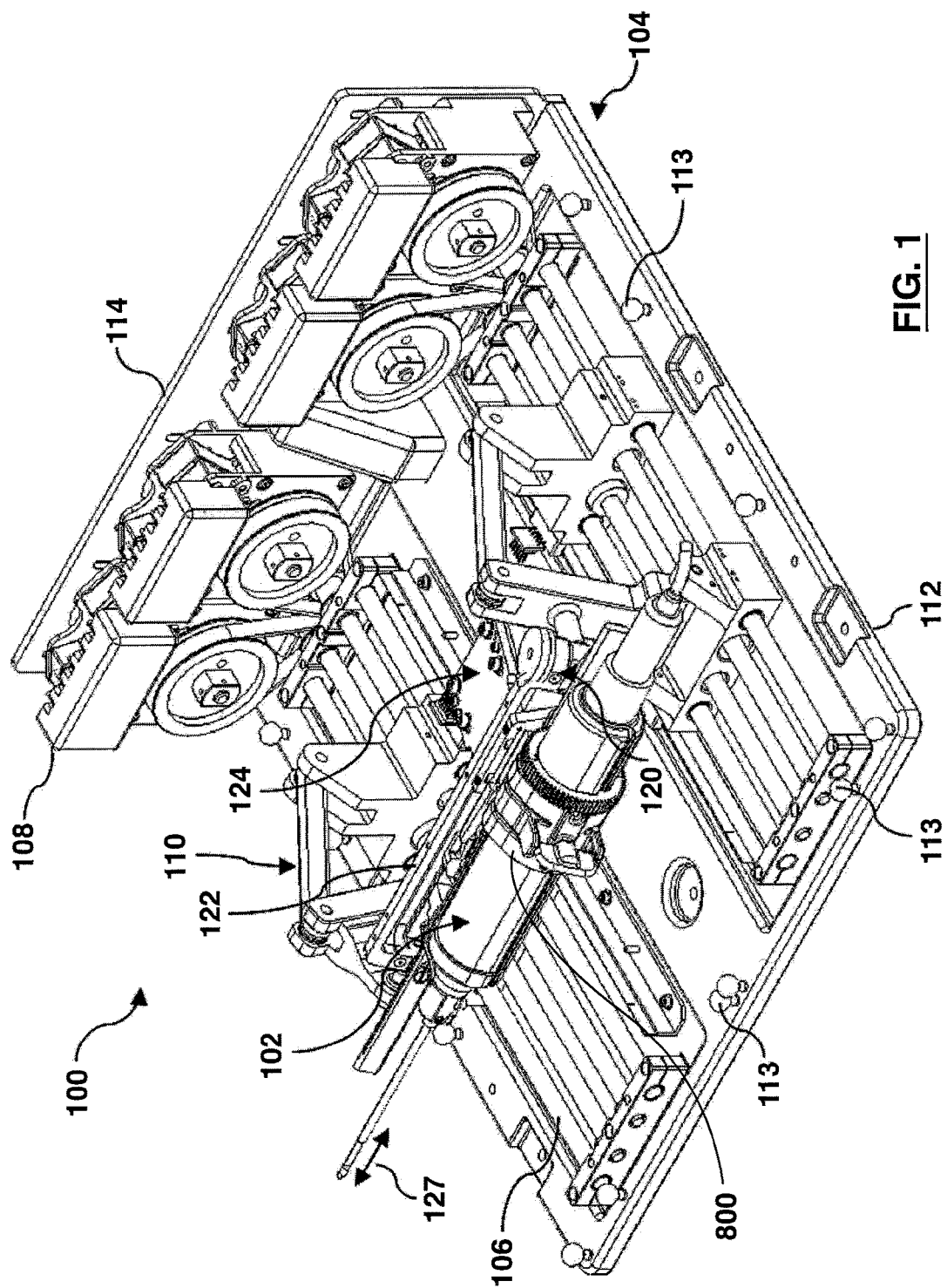
FIG. 1 is a perspective view of a medical insertion device in accordance with embodiments of the present invention.

Reference is now made to FIG. 1, which shows medical insertion device 100 in accordance with some embodiments of the present invention. Generally, medical insertion device 100 can be used in conjunction with an imaging system (not shown here), such as a magnetic resonance imaging (MRI) system, when the imaging system is in use.

Medical insertion device 100 can include frame 104, which can at least partially form a housing of medical insertion device 100. Medical insertion device 100 further includes linear slide assembly 106 mounted or connected to frame 104. Medical insertion device 100 further includes rotary drive assembly 108 for generally driving the linear slide assembly 106, and a carriage assembly 110 for moving along the linear slide assembly 106.

Frame 104 can include a baseplate 112 and a drive support plate 114 connected thereto to at least partially form a housing of medical insertion device 100. In an embodiment, the frame can include a wall(s), such as a front wall, side walls, a back wall, a top cover, and a bottom wall for protecting components of the medical insertion device, such as from dust or from a patient's bodily fluids, or for strengthening the structure of medical insertion device as required or desired. Frame 104 can also include drive plate strengthening brackets (not shown) for strengthening the connection between baseplate 112 and drive support plate 114 as required or desired. The front wall can define an opening for operation of components of the invention, as described further below.

In further embodiments, the frame can be integrated into or forms part of a frame that houses (not shown here) the imaging system (not shown here) with which medical insertion device interacts. The frame can be panel-shaped to fit within restricted environments having a limited height. The medical insertion device can be designed to act cooperatively with an imaging device according to various embodiments of the invention. For example, it can be sized to fit underneath the headrest of a patient support structure that maintains the patient in a face-down position for MRI breast imaging. This is an additional constraint on the space requirements imposed by MRI environment, including, but not limited to, the size and shape of the MRI patient bed and the dimensions of the MRI bore.

Linear slide assembly 106 can be connected to frame 104 at baseplate 112. The linear slide assembly can be connected to the frame by any means known in the art, such as welding, bolting, or riveting.

The medical insertion device can support, control and drive a medical instrument and/or a cannula as described further below. The medical insertion device can generally be used to retain, position, and effect insertion of the medical instrument and/or cannula into a patient. The medical insertion device can generally provide a variety of degrees of freedom, including linear, angular and/or rotational degrees of freedom, for positioning the medical instrument and/or the cannula prior to insertion of the medical instrument and/or the cannula into the patient. A tool mount adaptor may be coupled to the medical insertion device to secure the medical instrument to the medical insertion device. The medical insertion device can also include a sensor(s), such as a force sensor(s), for detecting the tissue being penetrated and for preventing accidental excursion into an incorrect tissue, such as a chest wall. The linear slide assembly can function to position and/or orient the medical instrument and/or cannula for insertion into a patient.

With reference to FIG. 1, medical insertion device 100 can further include a rotary drive assembly 108 mounted to drive support plate 114 for generally driving linear slide assembly 106, and a carriage assembly 110 for moving along linear slide assembly 106. Rotary drive assembly 108 can drive linear slide assembly 106 to different positions and configurations, thereby orienting medical instrument 102 and/or cannula 103 for insertion into a patient. The linear slide assembly can also be driven by direct linear drives attached directly to the slide assembly. This could be done with piezoelectric motors actuated against a linear slide assembly mounted to the frame or medical insertion device housing. Other means of operating the linear slide assembly would be readily apparent to the skilled person.

A carriage assembly can generally support and control a cannula carriage according to various embodiments of the invention, as described further below. With reference to FIG. 1, carriage assembly 110 can include elongate mounting arm 120, wherein mounting arm 120 includes an insertion track 122, which runs along a length of the mounting arm 120. Carriage assembly 110 can further comprise insertion carriage 124, which can be slideably mounted to insertion track 122. Insertion carriage 124 can include a mechanism (not shown) which can propel insertion carriage 124 along the insertion track 122. The mechanism can be any suitable mechanism known in the art, such as a pneumatic or piezoelectric motor, if MRI compatibility is required, or an inductive, or other similar electric, motor. Generally, movement of insertion carriage 124 along insertion track 122 can cause medical instrument 102 to move along insertion axis 127.

In the example shown, insertion track 122 can define insertion direction 127. In some example embodiments, components of the carriage assembly can include a force sensor(s) to detect the tissue being penetrated, and for prevention of accidental excursion into the incorrect tissue (e.g. a chest wall). In some embodiments, the alignment of the insertion axis can be confirmed before insertion via fiducial targets mounted either on the medical insertion device 100 or on the attached medical instrument. In alternative embodiments, fiducial targets can be mounted on a separate component that integrates with the robotic manipulator system or medical insertion device. For example, fiducial targets can be mounted onto a patient support, such as a table that a patient lies on during an MRI procedure. Motion can then be easily limited to along the confirmed axis during any contact with the patient.

In some embodiments, the baseplate can include alignment fiducials or other alignment markers for tracking the location of components of the medical insertion device relative to an absolute coordinate reference frame. The alignment fiducials provide an "absolute" or "global" reference frame for the system to which all real and virtual representations can be associated. For example, in FIG. 1, baseplate 112 can include alignment fiducials 113 for tracking the location of components of medical insertion device 100 relative to an absolute coordinate reference frame when viewing virtual representations, such as when using an imaging system (not shown here) to assist with a medical procedure. Alignment fiducials 113 can be associated with a variety of locations, such as the location of medical instrument 102 or cannula 103 itself, for correlation or registration purposes, as would be understood by those skilled in the art. Alternatively, alignment fiducials 113 attached to specific reference locations on the baseplate 112 can be used along with known or measured positions of the subcomponents of medical insertion device 100 to calculate the position of medical instrument 102 or cannula 103. These positions could be determined, for example, using medical images, encoders associated with the moving sub-components of the medical insertion device, or by some other means as would be understood by those skilled in the art. In some example embodiments, the alignment fiducial can include MR molecular tagging, which results in an increased conspicuity for accurate identification of the fiducial in MR images.

Figure 2:
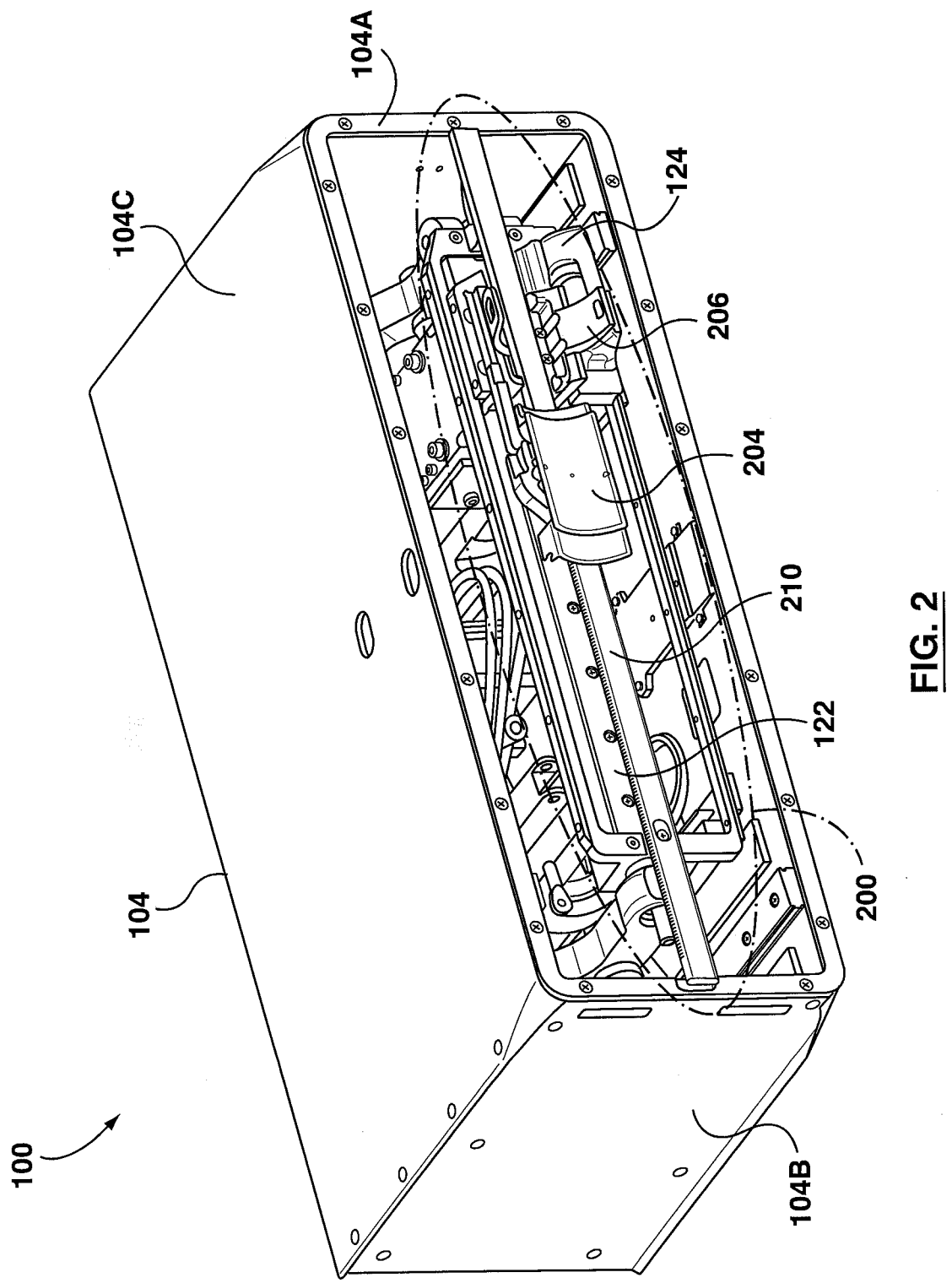
FIG. 2 is a perspective view of a medical insertion device according to various embodiments of the invention.
Figure 3:
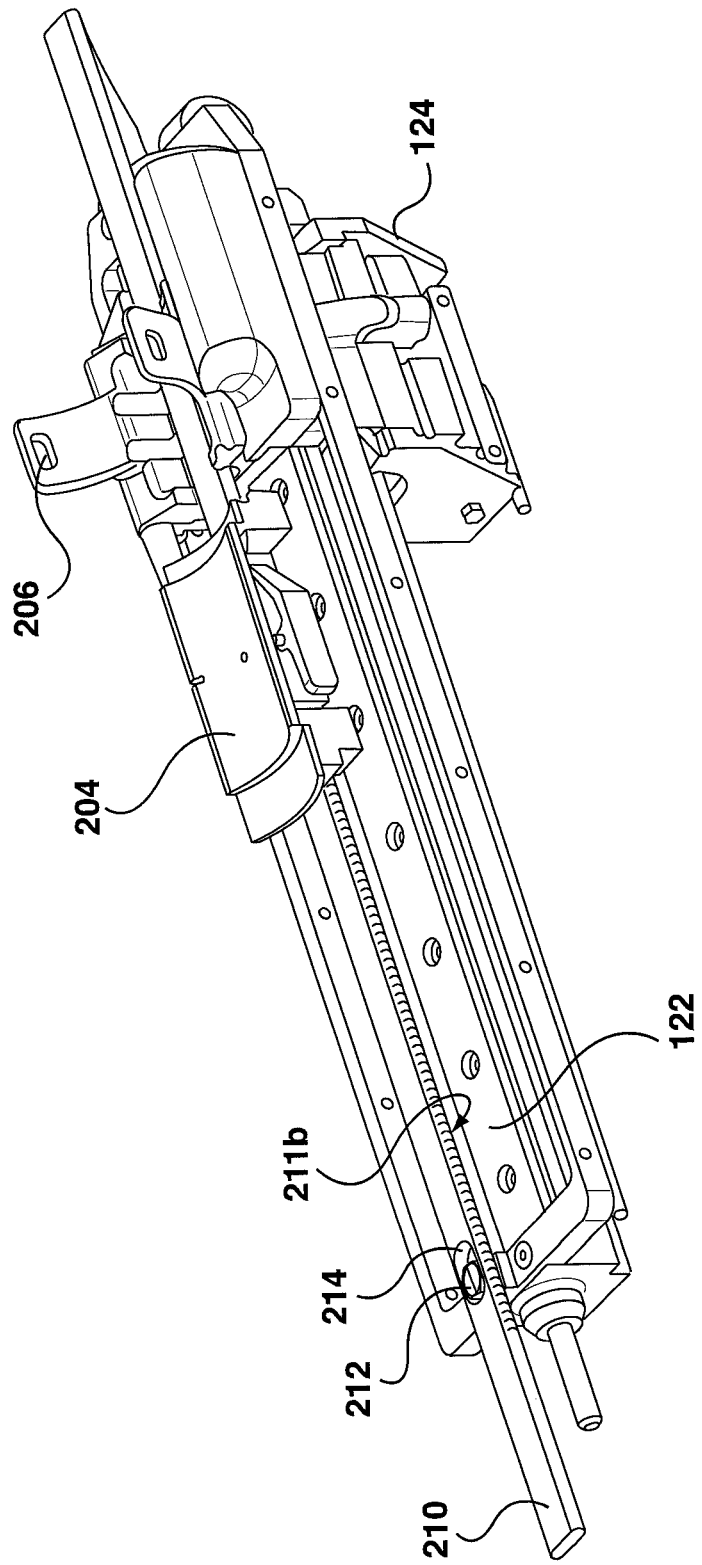
FIG. 3 is a perspective view of an end effector assembly isolated from the medical insertion device of FIG. 2, according to various embodiments of the invention.
Figure 4:
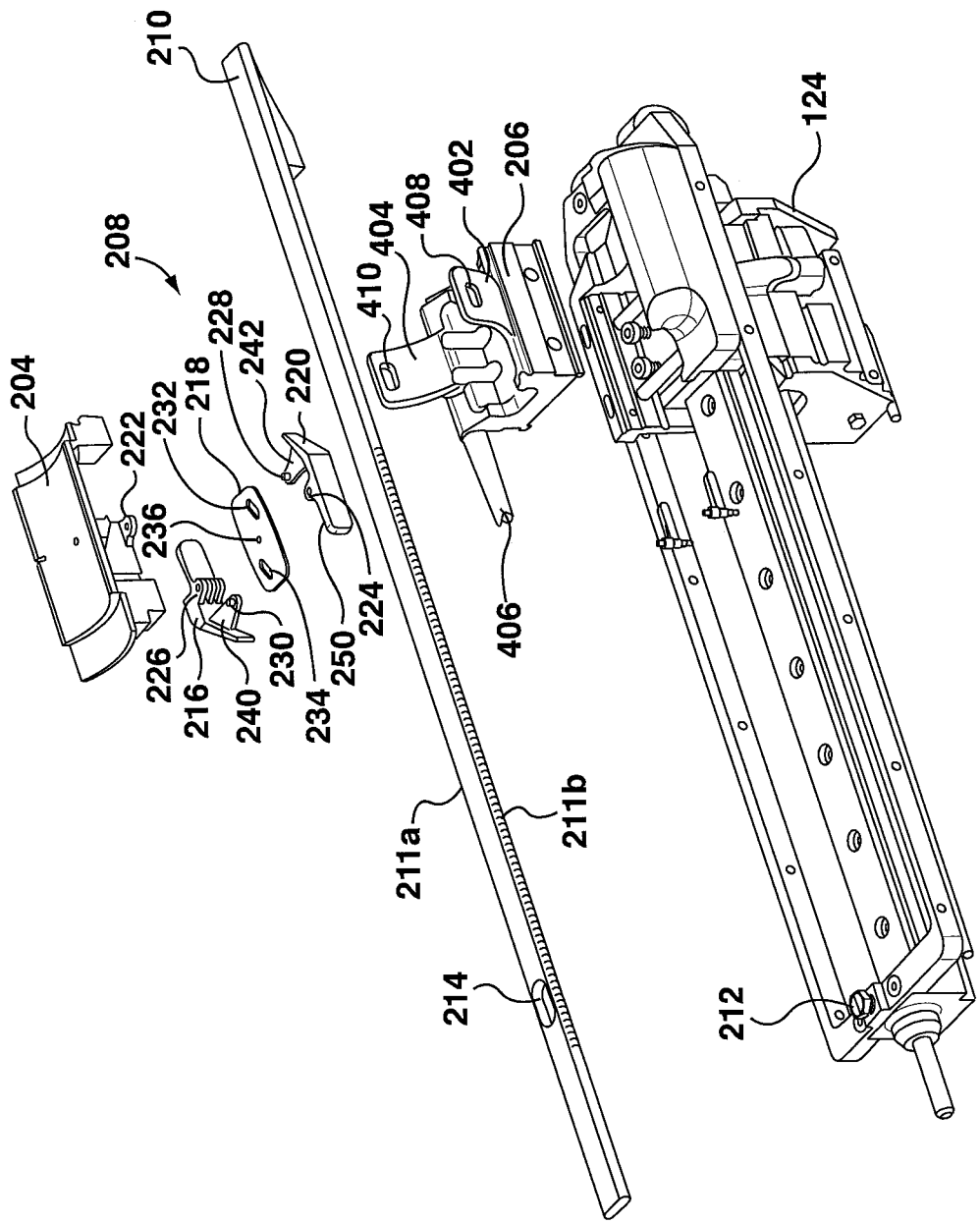
FIG. 4 is an exploded view of the end effector assembly shown in FIG. 3.
Figure 5:
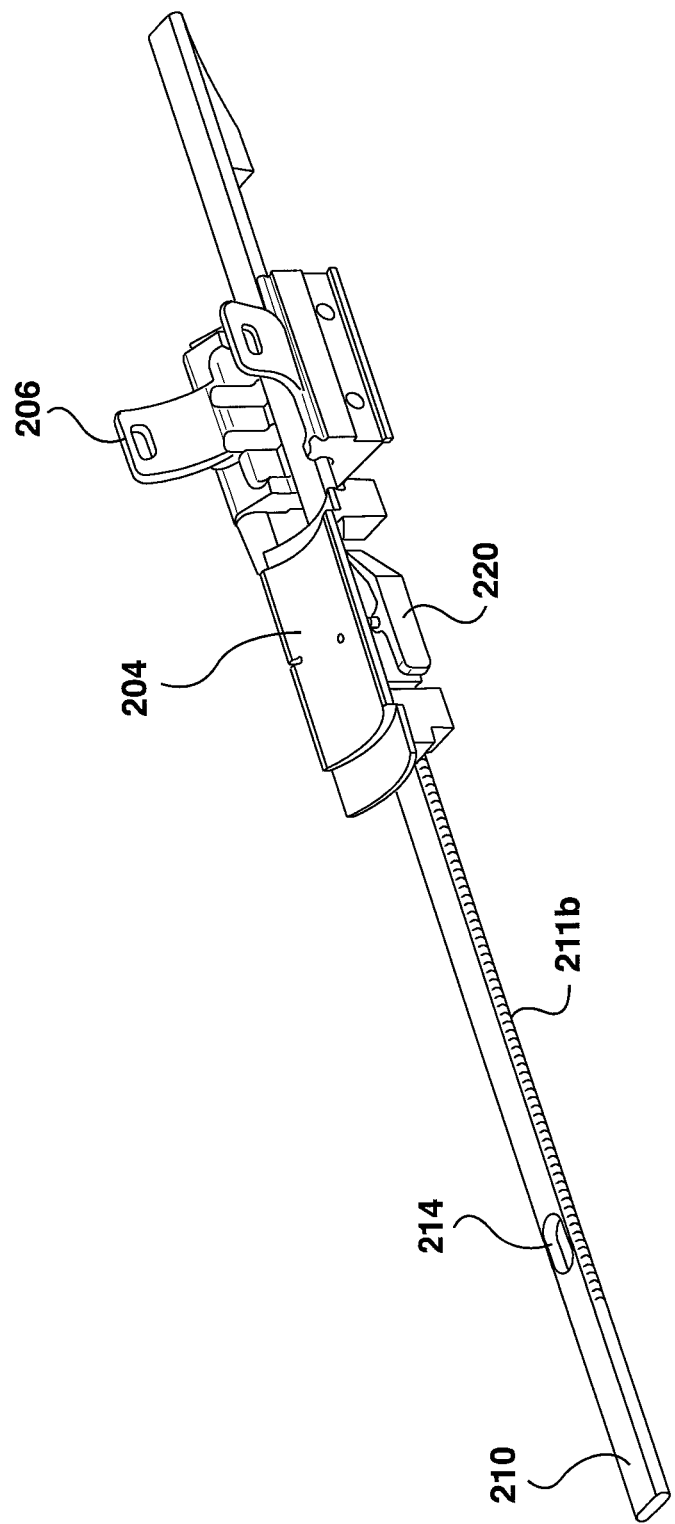
FIG. 5 is a perspective view showing some components of a cannula holder assembly isolated from the medical insertion device of FIG. 2, according to various embodiments of the invention.
Figure 6:
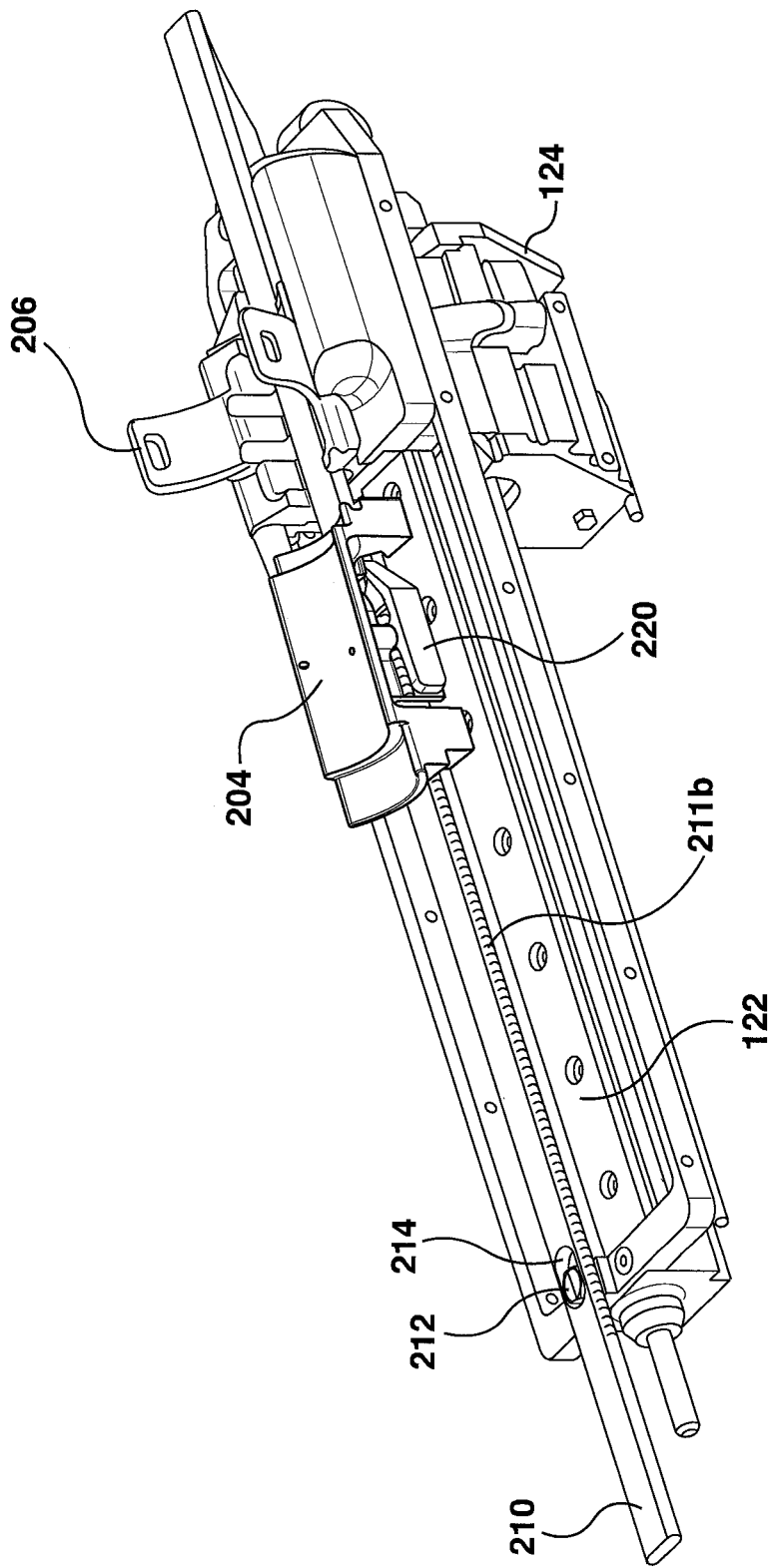
FIG. 6 is a perspective view showing the end effector assembly of FIG. 3 according to various embodiments of the invention.

Referring to FIG. 2, an alternate embodiment of the medical insertion device is depicted. In this embodiment, linear slide assembly 106 is folded in order to provide medical insertion device 100 in a more compact form. In this embodiment, carriage assembly 110 can support the end effector assembly 200 (described further below) through an opening defined in front wall 104A such that end effector assembly 200 is free of the drive assembly components. Further, in this configuration, the medical instrument (not shown) can be operated as a side mount, where the medical instrument is attached to the medical insertion device 100 generally from a direction that is perpendicular to front wall 104A. This configuration can allow accessing a patient and exchanging medical devices and the like simpler and safer, with less chance to unintentionally interact with the structural and moving components of the medical insertion device 100. The general function of the medical insertion device 100 has not been changed in this alternate configuration. For example, in this embodiment, the basis for motion and positioning of medical instrument 102 is a function of the relative position of four independent joints, mounted with two at each end of the end effector assembly 200 and one motor to allow motion along the end effector assembly 200 in the insertion/retraction direction 127. With regard to the method of tool attachment (side loading instead of rear loading), the direction of attachment is orthogonal to the insertion axis to reduce any chances of moving the medical instrument toward the patient unintentionally. In addition, this direction allows for a medical instrument changing system to be added more easily and simplifies the design of such a medical instrument changing system. With such an addition, the medical instrument changing system can be constructed such that the manipulator drives to the position where it picks up the medical instrument, and then the orthogonal 'stroke' to install the medical instrument would be short when compared to rear loading along the insertion axis.

Referring to FIG. 2, as well as FIGS. 3, 4, 5, 6, 7A, and 7B, an end effector assembly according to embodiments of the present invention will now be described. An end effector assembly, generally speaking, can be an assembly that supports and at least partially controls a medical instrument and/or cannula for insertion into a patient along the insertion axis. In FIGS. 2, 3, 4, 5, 6, 7A and 7B, end effector assembly 200 can comprise a cannula holder assembly which comprises cannula track 210. Cannula track 210 can generally extend along a length of the medical insertion device. Cannula track 210 can define fastener opening 214, through which fastener 212 can be inserted to fasten cannula track 210 to carriage assembly 110. Cannula track 210 can be fastened to carriage assembly 110 in any fashion known to the skilled person, as long as the functions of the end effector assembly according to the present invention are not substantially impeded. Cannula holder assembly can further comprise a cannula carriage which comprises cannula holder mount 204. End effector assembly 200 can further comprise end effector interface 206, which can operably interact with cannula holder mount 204, as described further below.

Cannula holder mount 204 can be slideably mounted to cannula track 210 by any mechanism known in the art. In the embodiment shown, cannula track 210 can define sets of teeth, e.g., notches 211, along its opposing elongated sides. The cannula carriage can further comprise a demobilizer. In a demobilization mode, the demobilizer can be adapted to restrict movement of the cannula carriage along the cannula track and in a mobilization mode allows movement of the cannula carriage along the cannula track. In some embodiments, the demobilizer can use a lever mechanism to engage or disengage the notches along the sides of the cannula track to restrict or allow movement of the cannula carriage along the cannula track. In some embodiments, the demobilizer can be, for example, movement lock 208, which can comprise guide plate 218 and side tabs 216 and 220. Side tabs 216 and 220 can comprise side tab fastening appendages 226 and 224 respectively for rotatably fastening each side tab to cannula holder mount 204 via cannula holder mount fastening appendages 238 and 222 respectively, each defined on the underside of cannula holder mount 204. Side tabs 216 and 220 each also define pivots 230 and 228 respectively and pawls 240 and 242 respectively.

Guide plate 218 defines guide plate openings 232 and 234 and fastening pivot 236. Fastening pivot is rotatably fastened to cannula holder mount 204. Each guide plate opening 232 and 234 slidably engage with pivots 228 and 230 respectively.

Figure 7A:
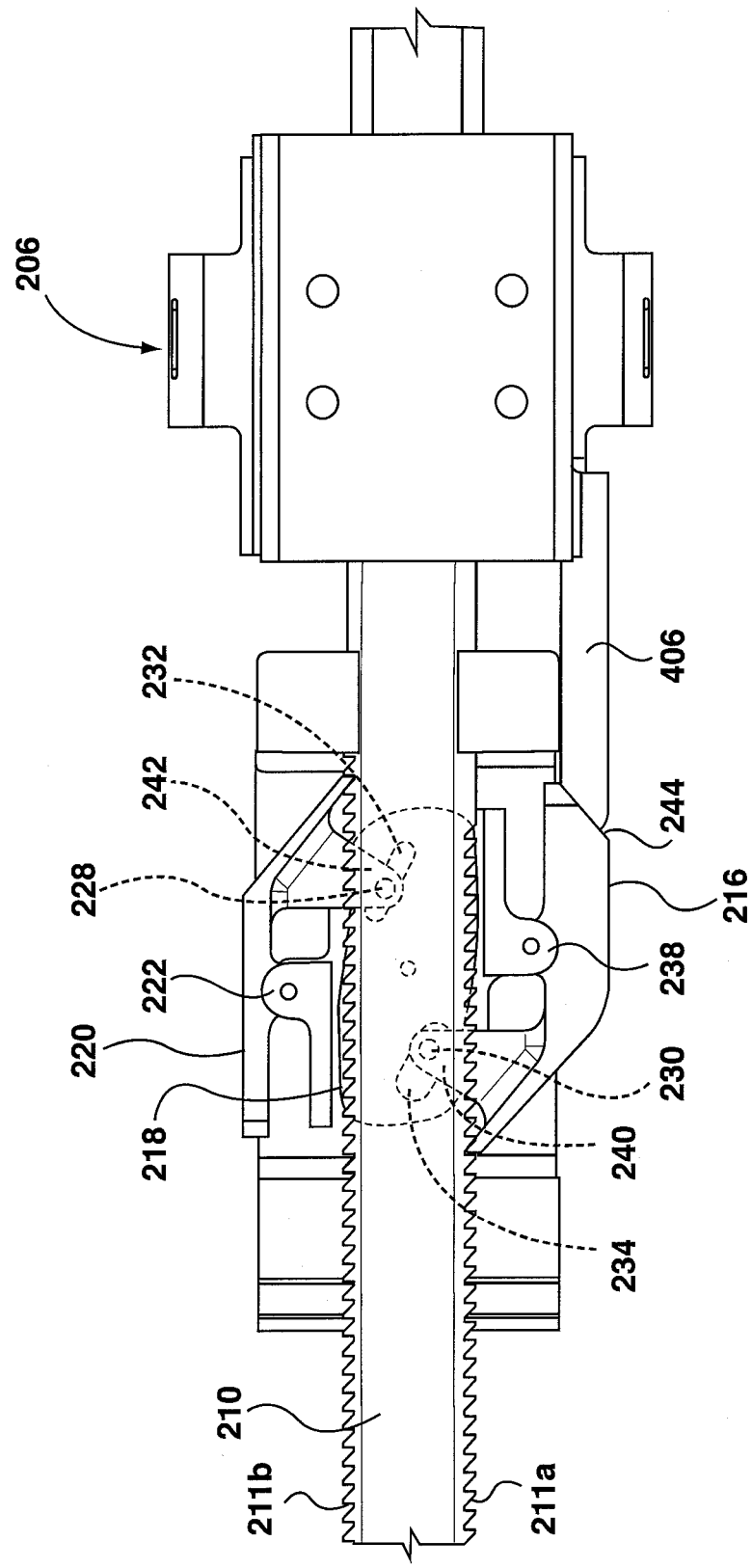
FIGS. 7A and 7B are views from the underside of the end effector assembly of FIG. 3 showing locked and unlocked positions of a movement locking mechanism.
Figure 7B:
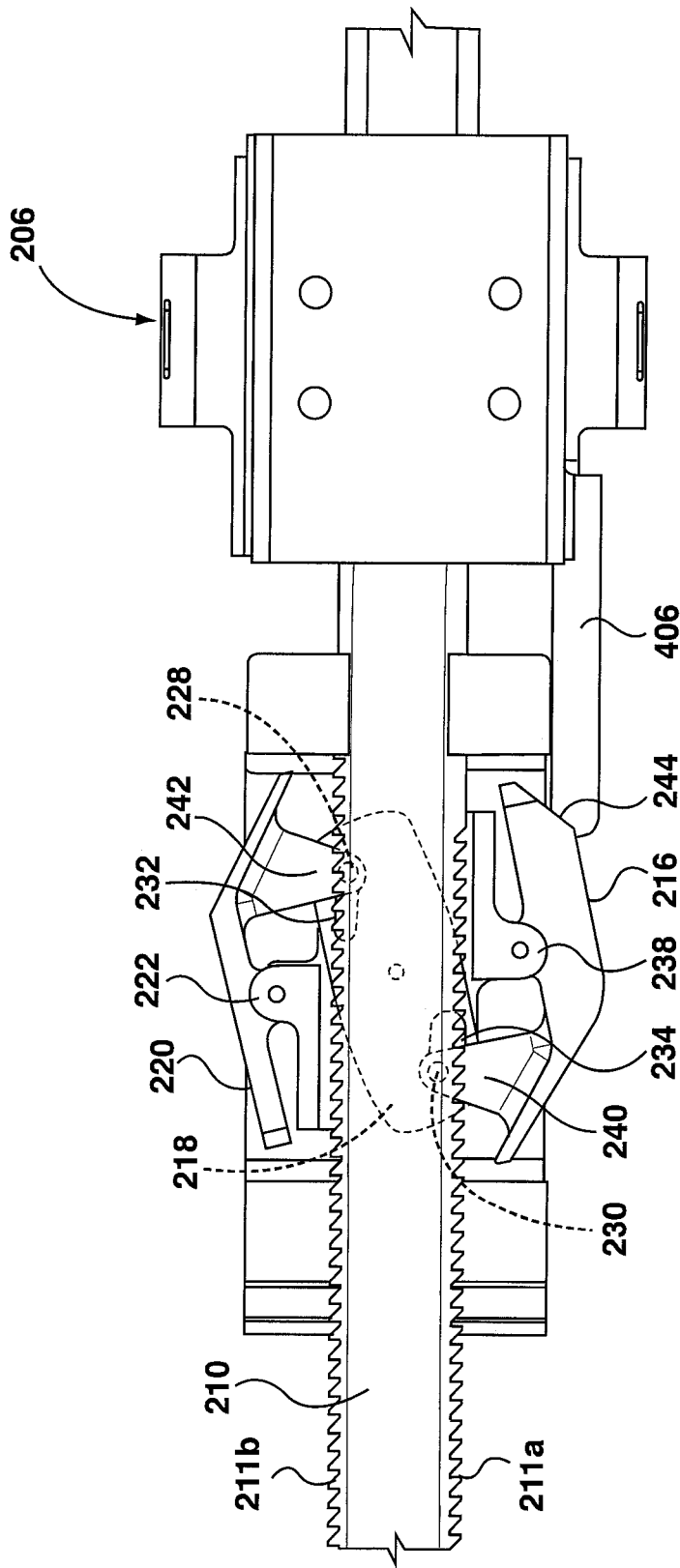
Figure 8:
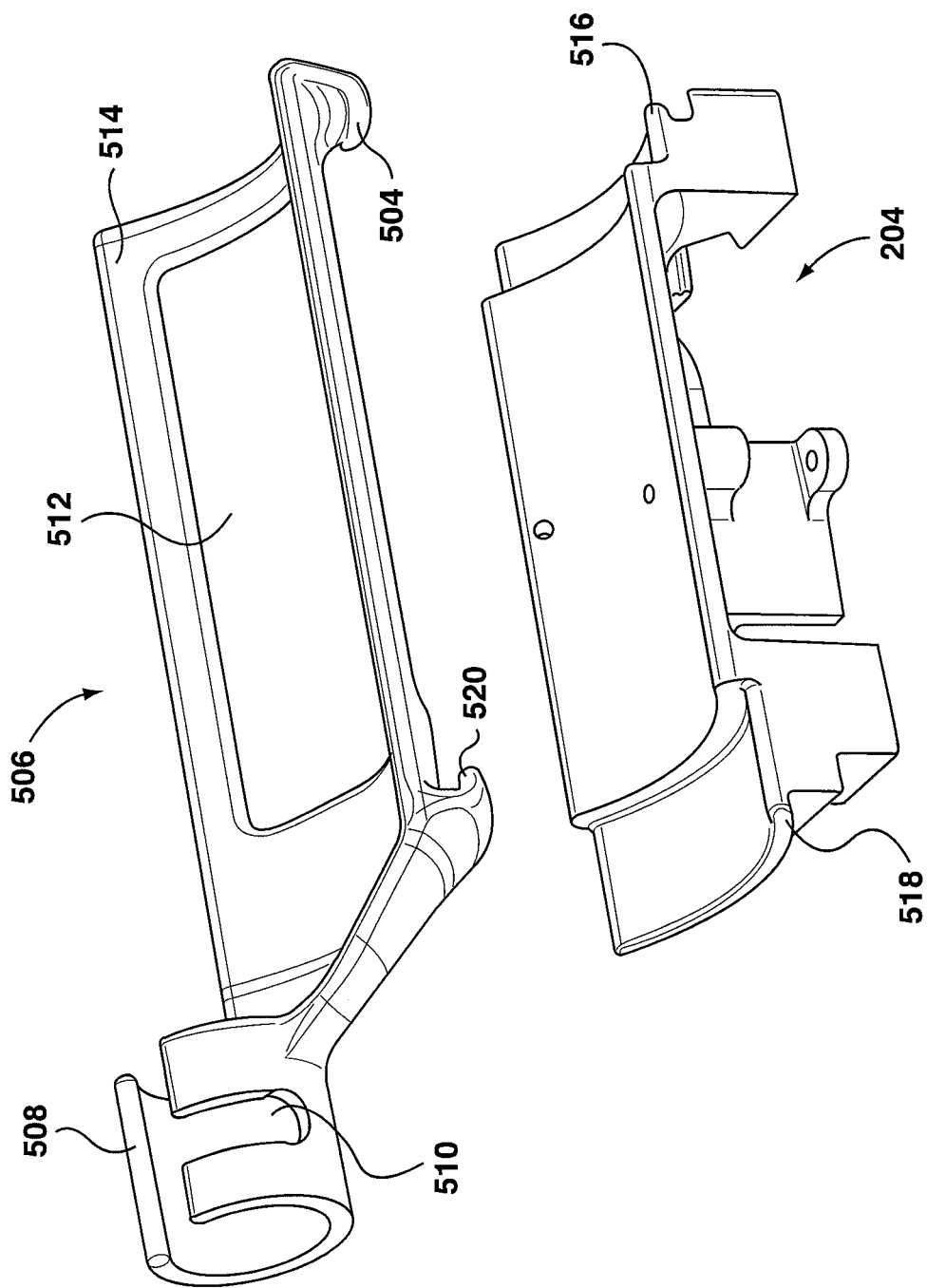
FIG. 8 is a perspective view of a cannula holder to be coupled to a cannula holder mount according to various embodiments of the invention.
Figure 9:
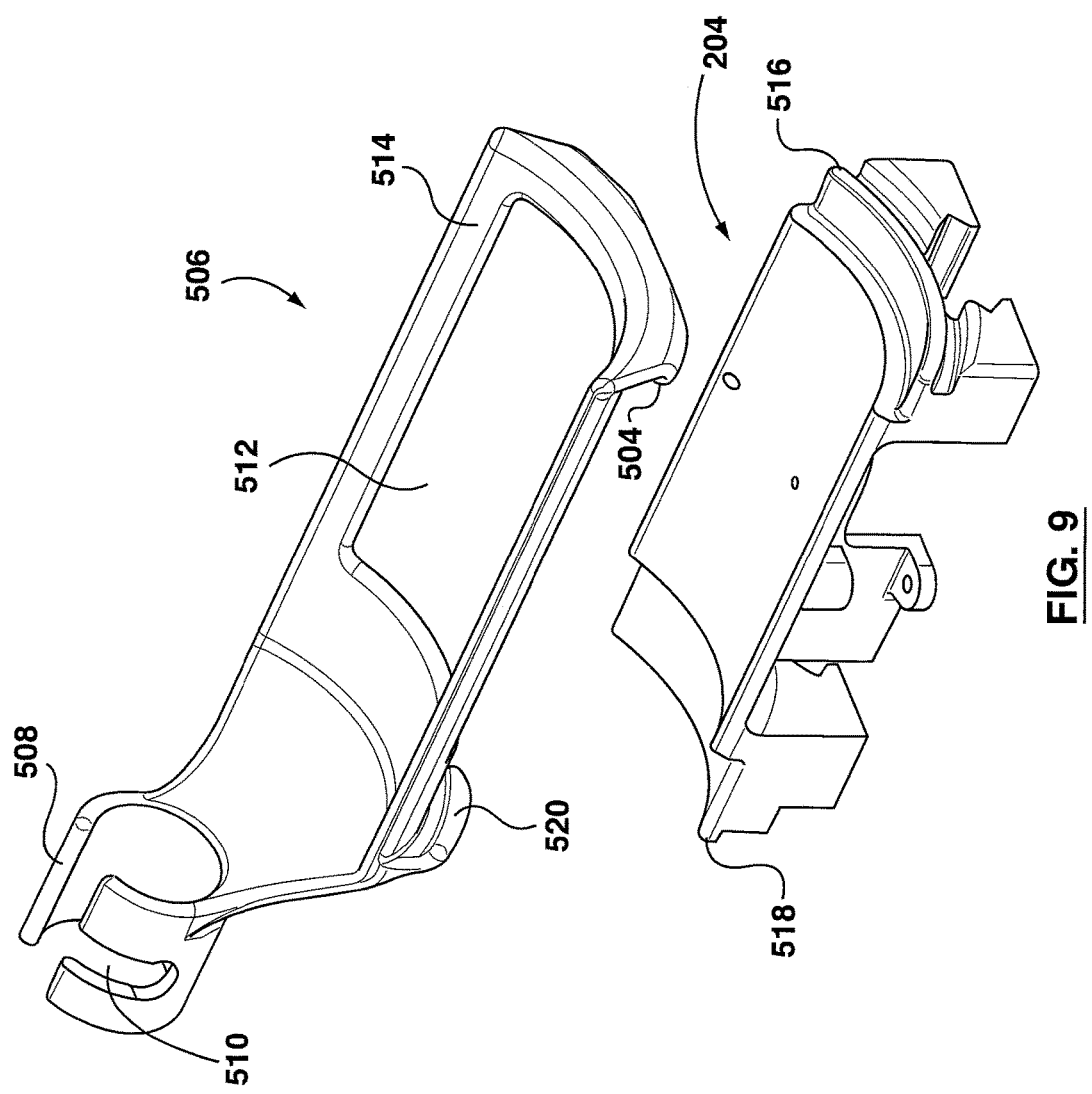
FIG. 9 is another perspective view of a cannula holder to be coupled to a cannula holder mount according to various embodiments of the invention.
Figure 10:
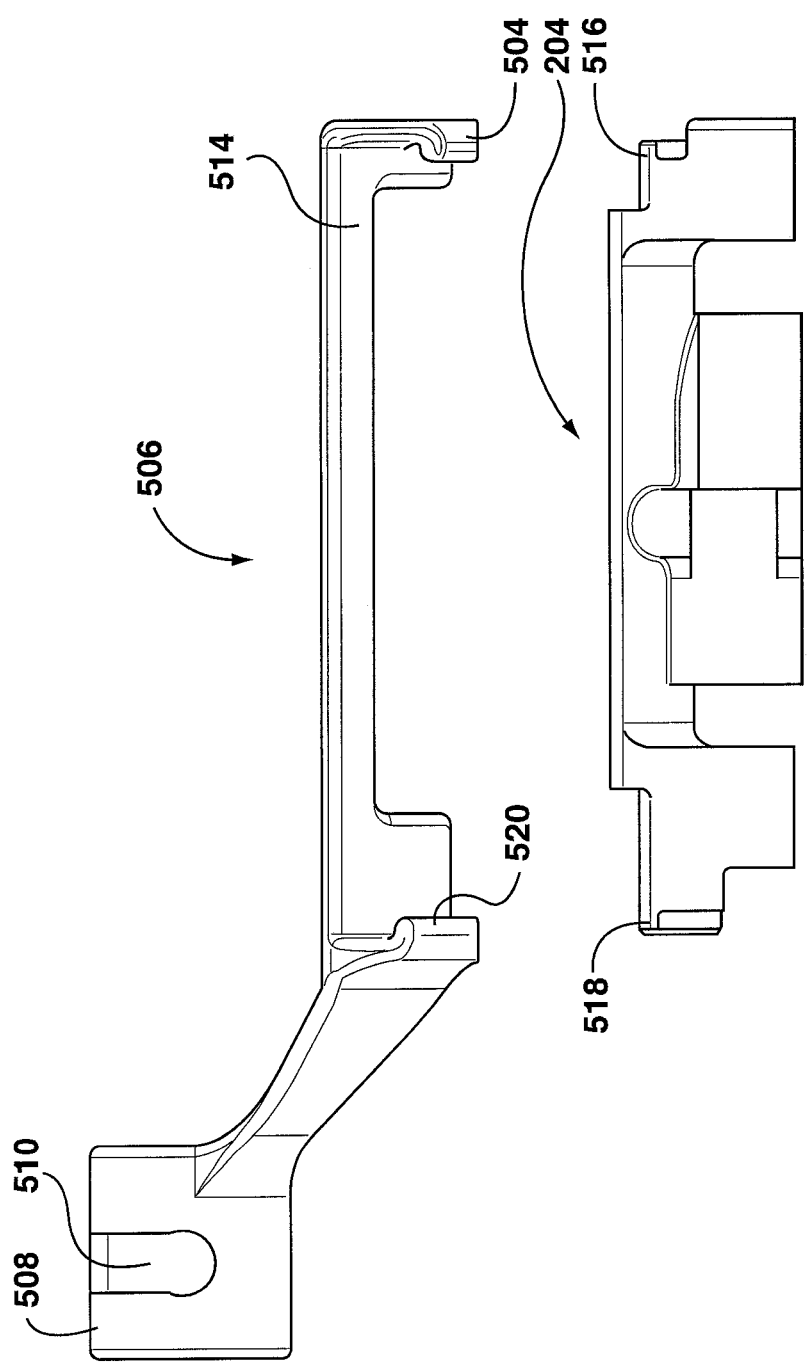
FIG. 10 is a side view of a cannula holder to be coupled to a cannula holder mount according to various embodiments of the invention.

Referring to FIGS. 7A and 7B, movement lock 208 is shown assembled and fastened to cannula holder mount 204 and cannula track 210, viewed from the underside of cannula holder mount 204 (cannula track 210 is transparent for viewing purposes). FIG. 7A shows the configuration where movement lock 208 is in the locked position. In the locked position, pawls 240 and 242 each engage a first set of teeth and a second set of teeth, respectively, e.g., notches 211a and 211b, in order to prevent cannula holder mount 204 from sliding in the insertion direction (towards the patient when in operation) or the retraction direction (away from the patient) along insertion axis 127. FIG. 7B shows the configuration where movement lock 208 is in the unlocked position. In the unlocked position each of pawls 240 and 242 do not engage notches 211a and 211b respectively. Movement lock 208 is biased to be in the locked position.

In some embodiments, the demobilizer can comprises a toggle mechanism for disengaging the first pawl from the first set of teeth when the second pawl is disengaged from the second set of teeth, and for disengaging the second pawl from the second set of teeth when the first pawl is disengaged from the first set of teeth. For example, movement lock 208 can be designed such that, if side tab 216 is moved in a manner that pawl 240 becomes disengaged from notches 211a, then pivot 230 will move along the oblong shape of guide plate opening 234. This movement will force guide plate 218 to pivot around fastening pivot point 236 such that the corresponding motion of guide plate opening 232 will cause pivot 228 to move along guide plate opening 232. The movement of pivot 228 will cause side tab 220 to pivot around side tab fastening appendage 224, which in turn can cause pawl 242 to disengage from notches 211b. Thus, causing either of side tab 216 or 220 to disengage from notches 211a or 211b respectively will cause the other tab to disengage from the respective notches through the action of guide plate 218.

Movement lock 208 can prevent cannula holder mount 204 from moving along either direction of cannula track 210. In some embodiments, notches 211a and 211b are not mirror images of each other through axis 127. Rather, notches 211a are notched in the opposite direction from notches 211b. Therefore, each of pawls 240 and 242 prevent cannula holder mount 204 from sliding along cannula track 210 in one direction, while allowing movement in the other direction.

In some embodiments, while pawl 240 generally prevents motion of cannula holder mount 204 in one direction of axis 127 and pawl 242 generally prevents motion in the opposite direction, it will be appreciated by the skilled person that movement lock 208 generally does not allow cannula holder mount 204 to move in either direction unless one or both pawls 240 and 242 are disengaged from the respective notches 211a and 211b. For example, guide plate opening 234 can be designed such that it is slightly larger than guide plate opening 232. This has the effect that if there is only partial movement of side tab 216 around pivot 230, only pawl 240 will disengage from notches 211a; therefore, motion will only be possible in one direction until side tab 216 is fully depressed, causing pawl 242 to disengage from notches 211b via action of guide plate 218 as described above.

In some embodiments, disengaging pawls 240 and 242 from the respective notches 211a and 211b can occur in more than one fashion. Firstly, side tab 220 defines lever 250, which can be manually pressed such that side tab 220 pivots around side tab fastening appendage 224 disengages pawl 242 from notches 211b. This would correspondingly disengage pawl 240 from notches 211a via guide plate 218 in the manner described above. This allows cannula holder mount 204 to be moved back and forth along cannula track 210 manually as desired.

In some embodiments, the insertion carriage can include a demobilizer-disengaging member adapted to set the demobilizer to a mobilization mode. In another embodiment, the end effector interface can include a demobilizer-disengaging member adapted to set the demobilizer to a mobilization mode. For example, another method of disengaging pawls 240 and 242 from the respective notches 211a and 211b can involve the interaction of end effector interface 206 with side tab 216, which can further comprise ramp 244.

End effector interface 206 can be fastened to insertion carriage 124 by screws, glue, or any other means known in the art. End effector interface 206 can define a space through which cannula track 210 can be disposed. End effector interface 206 can be mechanically powered through carriage assembly 110 through means such as a piezoelectric stepper motor housed inside the insertion carriage 124 such that end effector interface 206 can automatically move in either direction along cannula track 210. Other means could be an electric motor and/or gear or drive band mechanism. End effector interface 206 can comprise receiving members 402 and 404 and protrusion 406. Receiving members 402 and 404 can each define receiving member openings 408 and 410 respectively. Further, receiving members 402 and 404 can extend generally perpendicular to insertion axis 127 and can also at least partially define mounting tray 600. In operation, as end effector interface 206 is propelled along cannula track 210, protrusion 406 can engage ramp 244, which causes pawl 240 to disengage from notches 211a and allows cannula holder mount 204 to move in an insertion direction along axis 127. Once end effector interface 206 retreats from engagement with cannula holder mount 204, cannula holder mount 204 becomes locked at the location along cannula track 210 at which end effector interface 206 left it.

As described above, ramp 244 and guide plate opening 234 can be constructed such that only pawl 240 disengages from notches 211a, while pawl 242 remains engaged with notches 211b, when protrusion 406 engages ramp 244. This has the function of allowing only forward motion of cannula holder mount 204 when end effector interface 206 moves in an insertion direction along axis 127. Due to pawl 242 being engaged with notches 211b, this has the secondary function of ensuring that cannula holder mount 204 does not move backwards along axis 127 once end effector interface 206 retreats from engagement with cannula holder mount 204.

Figure 12A:
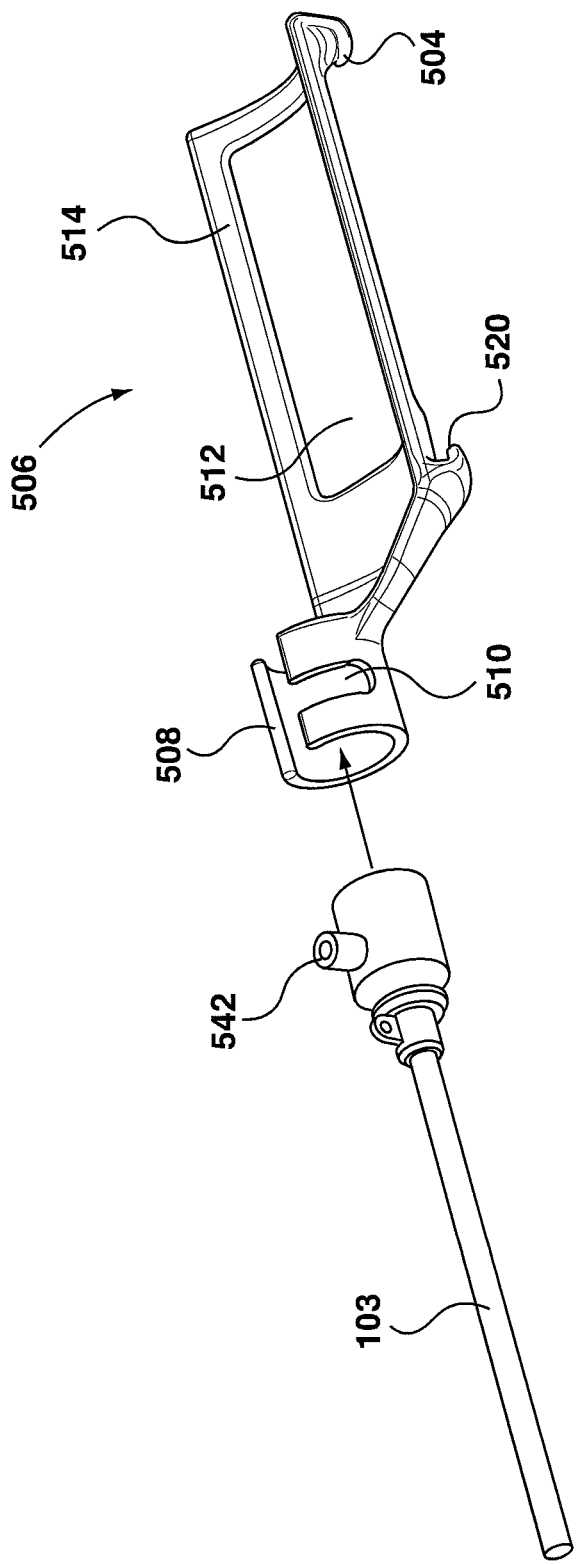
FIGS. 12A, 12B and 12C are perspective views showing insertion and locked positions of a cannula in the cannula holder shown in FIG. 8.
Figure 12B:
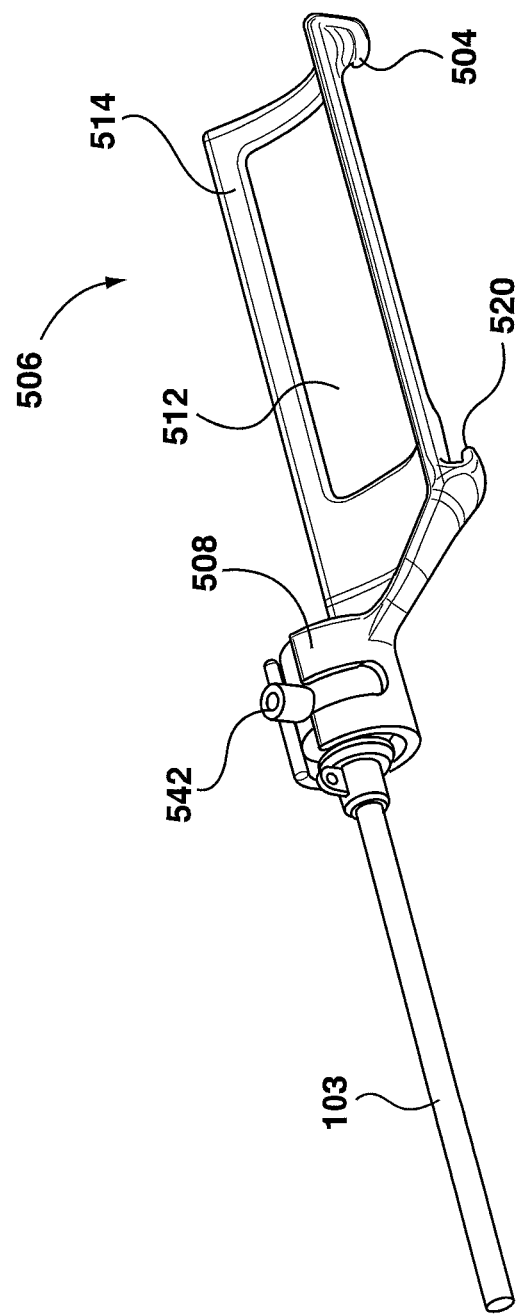
Figure 12C:
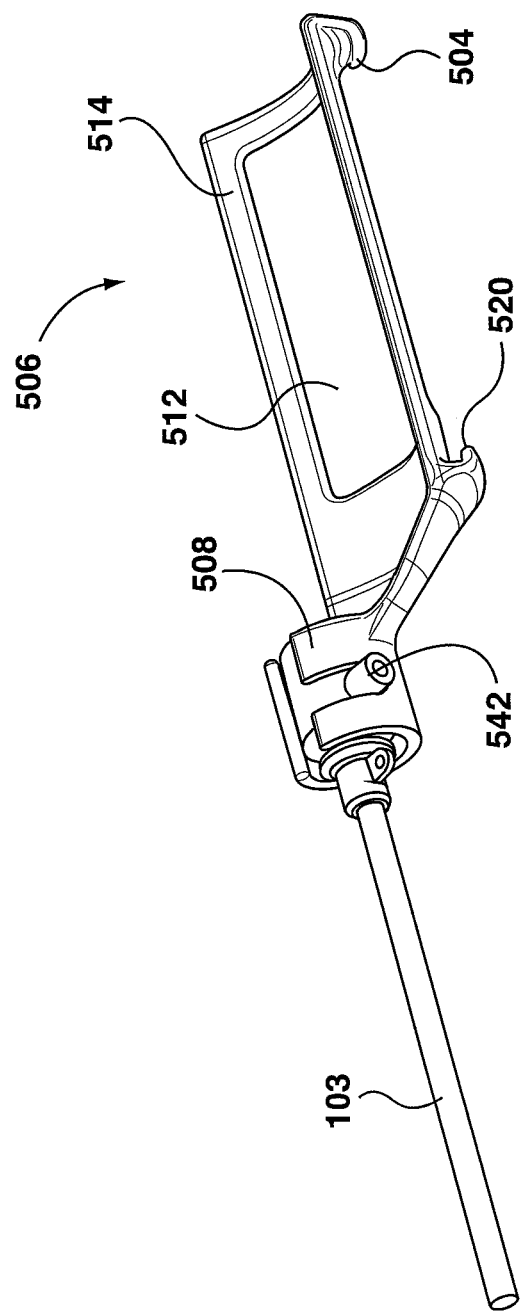

Referring to FIGS. 8, 9, 10, 11, 12A, 12B and 12C, the function the cannula holder mount will be further described. Cannula holder mount 204 can be adapted to receive cannula holder 506. Cannula holder 506 comprises securing mechanism 508, to which cannula 103 can be reversibly secured. In the embodiment shown, securing mechanism defines securing mechanism slot 510 which can assist in securing a cannula 103 to cannula holder 506. For example, as shown in FIGS. 12A, 12B and 12C, cannula 103 can define appendage 542, which can be adapted to securely engage with securing mechanism slot 510 when cannula 103 is secured to cannula holder 506. In the example embodiment, cannula 103 is shown in relation to cannula holder 506 in three positions: (i) ready to be positioned (FIG. 12A), (ii) positioned but not locked (FIG. 12B), and (iii) locked in place (FIG. 12C). Securing mechanism 508 can be designed to securely fit the dimensions of any cannula 103, such as the dimensions of the ATEC™ cannula. When properly fitted, cannula 103 is generally parallel to axis 127 and will travel only on this axis as cannula holder mount 204 moves along cannula track 210. When properly fitted, cannula holder 506 ensures that the cannula is positioned such that, for example, a needle of a vacuum assisted biopsy (VAB) tool can pass through the hollow middle portion of cannula 103.

Cannula holder 506 further comprises tray 514 which is generally shaped to allow passage of medical instrument 102. Tray 514 defines tray opening 512 which generally pieces together with a portion of cannula holder mount 204. Cannula holder 506 further comprises cannula holder attachments 504 and 520 on the underside of tray 514. Cannula holder attachments 504 and 520 can securely attach through a snap-fit to mating attachments 516 and 518, which are defined on generally opposing ends of cannula holder mount 204. Other methods of securing cannula holder 506 to cannula holder mount 204 will be readily apparent to the skilled person, and include pin/socket connectors, clips, wrap-around parts, friction fit, permanent or temporary adhesives, screws, and the like. Attaching cannula holder 506 to cannula holder mount 204 allows cannula 103, when secured to cannula holder 506, to move co-axially with and be controlled by the movement of cannula holder mount 204.

According to some embodiments of the invention, cannula holder mount 204 is not able to move without manual intervention. Other possible mechanisms recognized by the skilled person could involve implementing an independent actuator or motor to move cannula holder mount 204 without the need for manual intervention.

Figure 13:
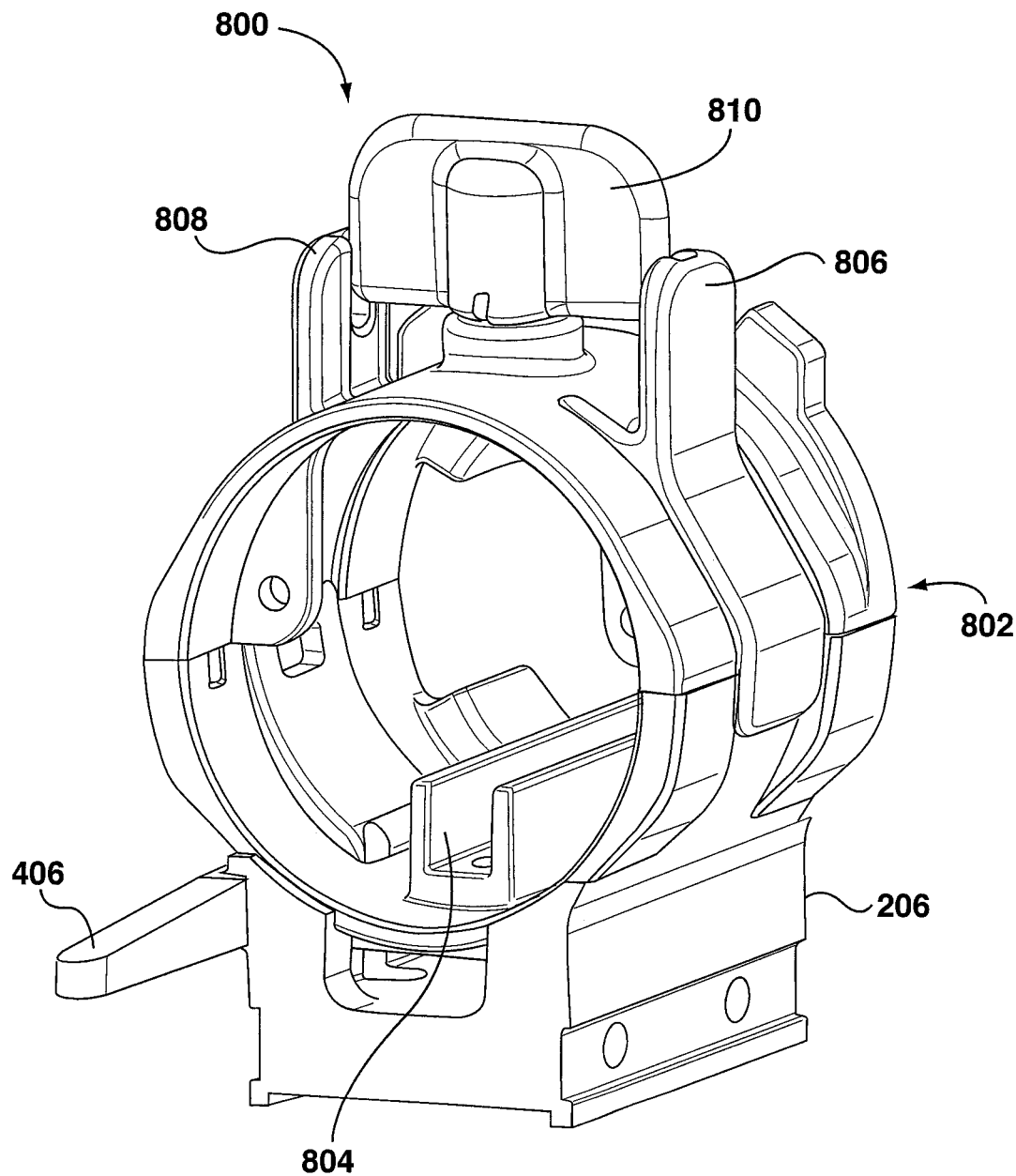
FIG. 13 is a perspective view of a tool mount adaptor according to embodiments of the present invention.
Figure 14:
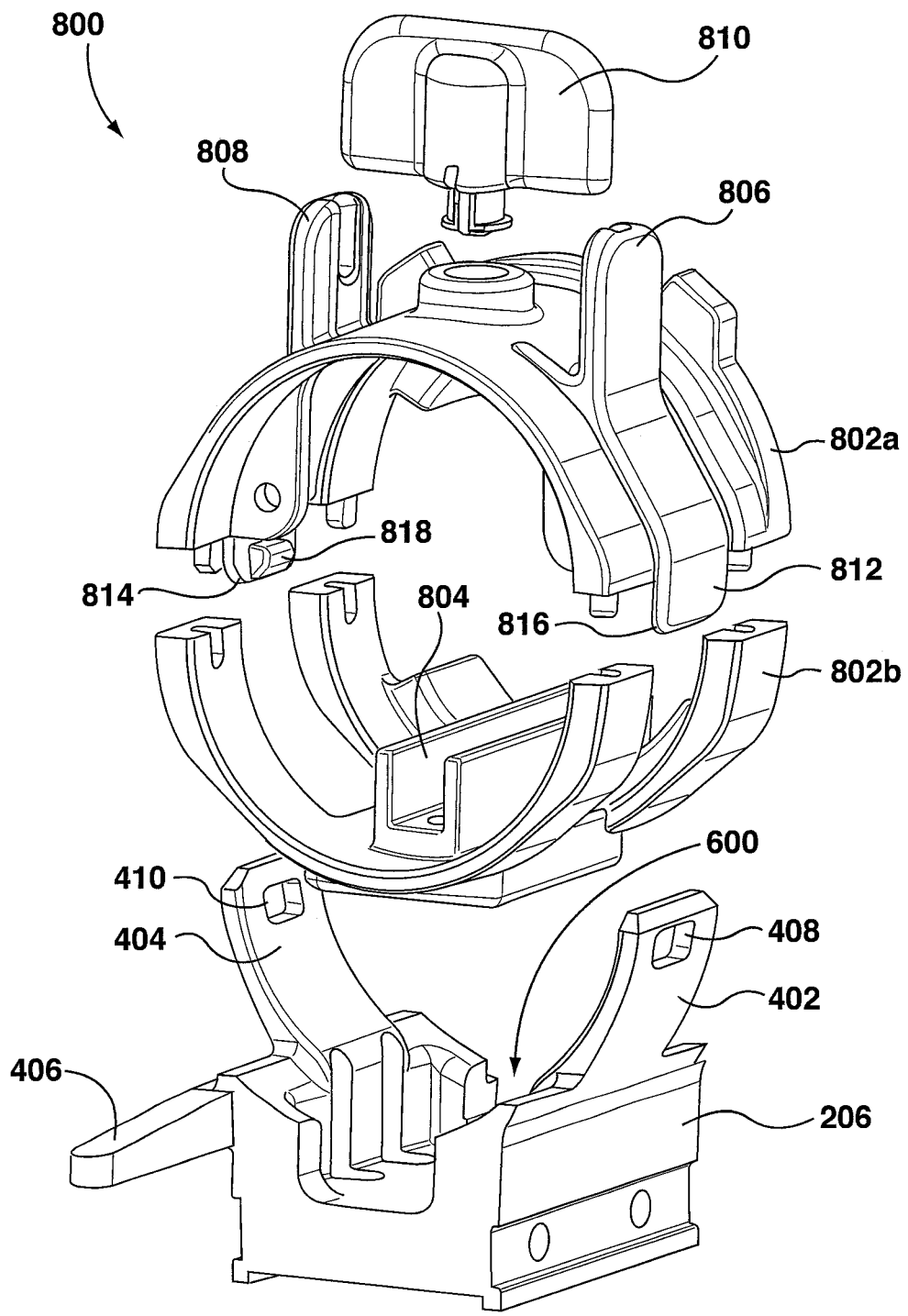
FIG. 14 is an exploded view of the tool mount adaptor shown in FIG. 13.

Referring to FIGS. 13 and 14, tool mount adaptor 800, which can releasably attach to end effector interface 206, will be further described according to another embodiment of the invention. Tool mount adaptor 800 can comprise collar 802, which can be comprised of more than one interconnecting piece. In the embodiment shown, collar 802 is comprised of pieces 802a and 802b, which can releasably couple to each other to form collar 802. Generally, tool mount adaptor 800 can function to operably connect medical instrument 102 to medical insertion device 100. Collar 802 can be releasably secured to medical instrument 102 or cannula 103 for attachment to mounting tray 600 of end effector interface 206. In an embodiment of the tool mount adaptor 800, the inner diameter of collar 802 may be, for example, about 41.8 mm. This diameter defines the maximum diameter of tool or medical instrument 102 that can be accommodated by the tool mount adaptor; alternately, increasing the size of the tool mount adaptor will consequently increase this diameter, allowing larger tools to be held at the expense of limiting range of motion due to collisions with the structure of the medical insertion device 100 or surrounding structure (e.g., the imaging system or patient). Collar 802 can attach to any suitable medical instrument, and can allow a variety of medical instruments to be operable with medical insertion device 100. In other embodiments, collar 802 can be integrated into medical instrument 102 for simplifying setup of medical instrument 102 for use with medical insertion device 100.

Figure 15A:
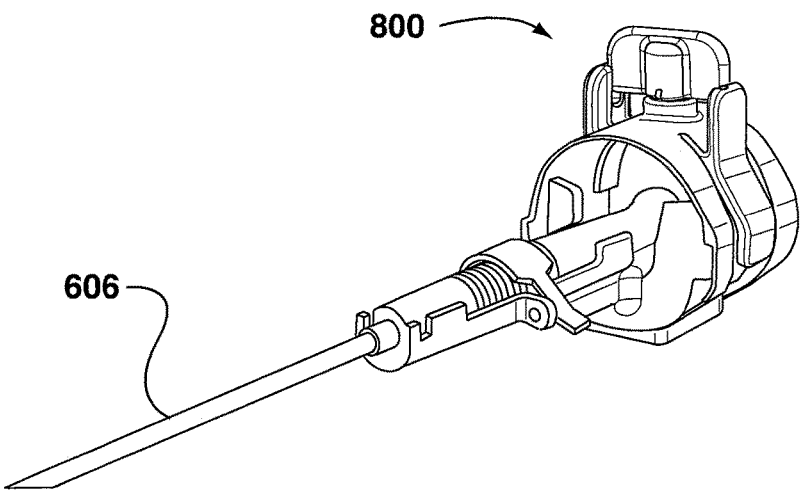
FIGS. 15A, 15B and 15C show various medical instruments secured by a tool mount adaptor according to various embodiments of the invention.
Figure 15B:
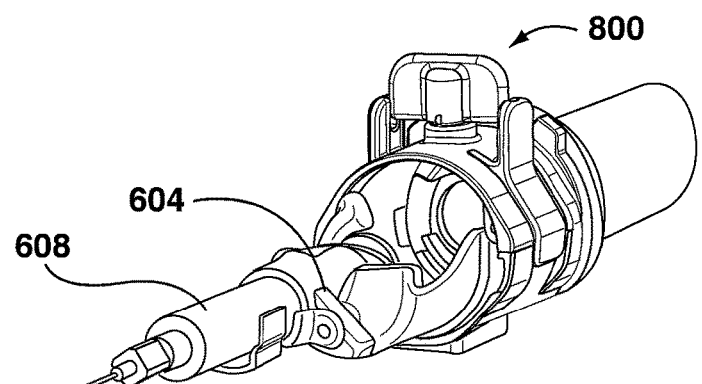
Figure 15C:
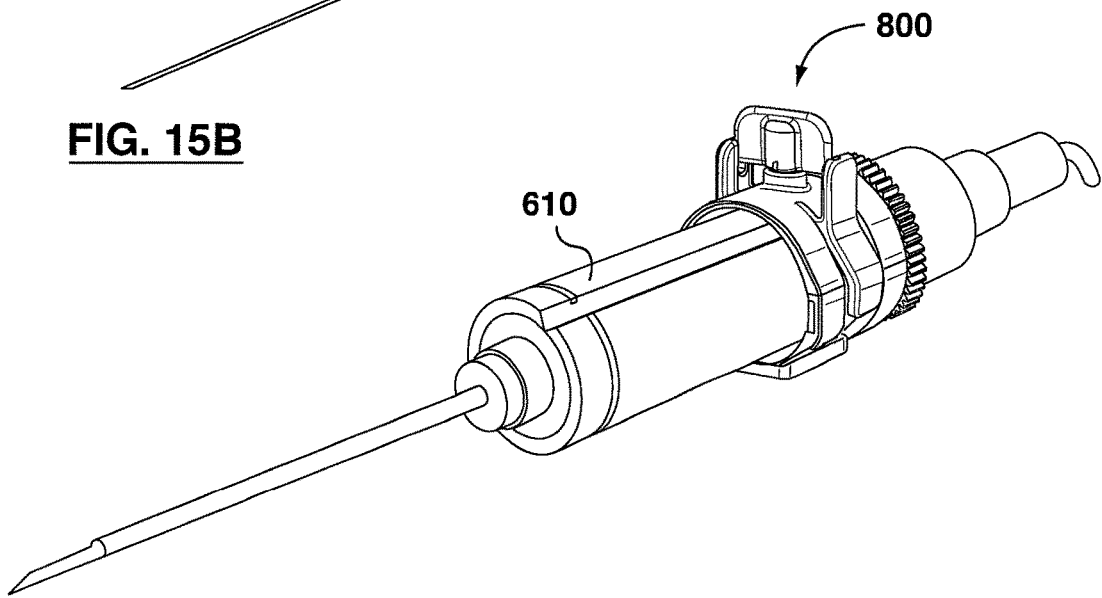

As shown in FIGS. 15A, 15B and 15C, collar 802 can be used to mount different medical instruments to medical insertion device 100 such as a trocar tool 606 (FIG. 15A), an anesthesia tool 608 (FIG. 15B), or a biopsy tool 610 (FIG. 15C). Other medical instruments or tools, such as needle based diagnostic or therapeutic devices such as ablative, fibre-optic, or other technologies, that fit within the collar 802 can be accommodated for use with medical insertion device 100 through an appropriately modified tool mount adaptor 800 as would be appreciated by a skilled person. For example, in FIG. 15B, tool mount adaptor 800 can include latch 604, which can secure, or aid in securing, anesthesia tool 608 to tool mount adaptor 800. The use of several tool mount adaptors 800 coupled to different medical instruments 102 could allow for an entire clinical procedure or aspects of a clinical procedure to be conducted robotically using medical insertion device 100.

Collar 802 can include tab members 806 and 808, which operably connect to connection ends 812 and 814, respectively. Connection ends each define nubs 816 and 818 on their inner surfaces. Upon connecting tool mount adaptor 800 to end effector interface 206, tab members 806 and 808 can be depressed inwardly generally towards each other in order to extend connection ends 812 and 814 outwardly and against the bias. Collar 802 can then be placed in mounting tray 600 and tab members 806 and 808 can be released, thereby allowing receiving member openings 408 and 410 to securely receive nubs 816 and 818. The skilled person would understand that variations are possible, for example, openings can be defined on the connection ends while nubs are defined on the receiving members. The skilled person would also understand that there are other methods of securing collar 802 to mounting tray 600 including, but not limited to, a screw and threaded hole fixture between aligned and touching parts of securing collar 802 and mounting tray 600, or a friction fit or tongue-and-groove construction.

In some embodiments, connection ends 812 and 814 and nubs 816 and 818 can be made, at least partially, from a resilient material such as a thermoplastic, thermoset plastic, or a composite material such as fibreglass or carbon fibre. In other embodiments, connection ends 812 and 814 can include hinges and can be spring-biased to maintain the engagement of connection ends 812 and 814 to receiving member openings 408 and 410.

As described above, mounting tray 600 can include receiving members 402 and 404, which can comprise of multiple "fingers", and not necessarily just single members as shown in the figures. Furthermore, receiving members 402 and 404, may or may not conform exactly to the shape of the medical instrument 102 and they can extend around medical instrument 102 to varying degrees (e.g., they are shown to extend over approximately half of the circumference of a cylinder in the embodiment shown in the figures). The exact dimensions of receiving members 402 and 404 will depend on the requirements of the specific embodiment of the invention.

In another embodiment, collar 802 can include lockout tab 810, which can prevent the accidental release of collar 802 from the mounting tray of end effector interface 206. When lockout tab 810 is in a securement mode, it can restrict the ability of an operator from disengaging connection ends 812 and 814 by limiting access to tab members 806 and 808. When lockout tab 810 is in instrument changing mode, it can allow an operator to disengage connection ends 812 and 814 by operating tab members 806 and 808. As will be understood by the skilled person, it can be possible for an operator to mount or remove medical instrument 102 with one hand. For example, an operator can hold a portion of medical instrument 102 generally near collar 802. The operator can then turn lockout tab 810 and then depress tab members 806 and 808 with his or her thumb and finger. Medical instrument 102 would then be released from medical insertion device 100. The skilled person will recognize that other means of preventing disengagement of connection ends 812 and 814 is also possible by methods such as, but not limited to, a cover over the entirety of operating tab members 806 and 808 that does not allow their operation.

As will have become apparent to the skilled person, collar 802 is designed to securely attach to a medical instrument 102 in order to allow quick fastening to medical insertion device 100. In some embodiments, multiple tool mount adaptors 800 can be on hand, each attached to a different medical instrument 102. This will allow quick and secure interchangeability during a procedure on a patient.

Tool interface feature 804 is shown as an example embodiment of features that may be fashioned into the interior surface of tool mount adaptor 800. Features such as tool interface feature 804 may be constructed to ensure a secure, slip-free, and consistent mounting of a medical instrument 102 in a specific manner, such that the tip of medical instrument 102 will always be in a known location relative to the end effector interface 206. It is understood by persons skilled in the art that the exact nature of a tool interface feature is dependent on the specific surface features medical instrument to which the tool mount adaptor is being designed to fit. These features can include, but would not be limited to, the variable shape of the housing and/or grooves or other features that consistently form part of the outer surface of the medical instrument. In some embodiments, the medical instrument is held securely in the tool mount adaptor such that the location of the tip of the tool can be calculated to a high degree of accuracy. In some embodiments, the medical instrument is held securely in the tool mount adaptor such that the location of the tip of the medical instrument can be calculated to a millimeter degree of accuracy or a sub-millimeter degree of accuracy. For example, the medical instrument is held securely in the tool mount adaptor such that the location of the tip can be calculated to a 2 mm degree of accuracy, a 1 mm degree of accuracy, a 0.9 mm degree of accuracy, a 0.8 mm degree of accuracy, a 0.7 mm degree of accuracy, a 0.6 mm degree of accuracy, a 0.5 mm degree of accuracy, a 0.4 mm degree of accuracy, a 0.3 mm degree of accuracy, a 0.2 mm degree of accuracy or a 0.1 mm degree of accuracy. In some embodiments, the medical instrument is held securely in the tool mount adaptor such that the location of the tip of the medical instrument relative to the tool mount adaptor deviates to a very small degree. For example, in some embodiments, the medical instrument is held securely in the tool mount adaptor such that the location of the tip of the medical instrument relative to the tool mount adaptor deviates less than 1 mm, less than 0.9 mm, less than 0.8 mm, less than 0.7 mm, less than 0.6 mm, less than 0.5 mm, less than 0.4 mm, less than 0.3 mm, less than 0.2 mm, less than 0.1 mm, less than 0.09 mm, less than 0.08 mm, less than 0.07 mm, less than 0.06 mm, less than 0.05 mm, less than 0.04 mm, less than 0.03 mm, less than 0.02 mm or less than 0.01 mm.

Figure 16:
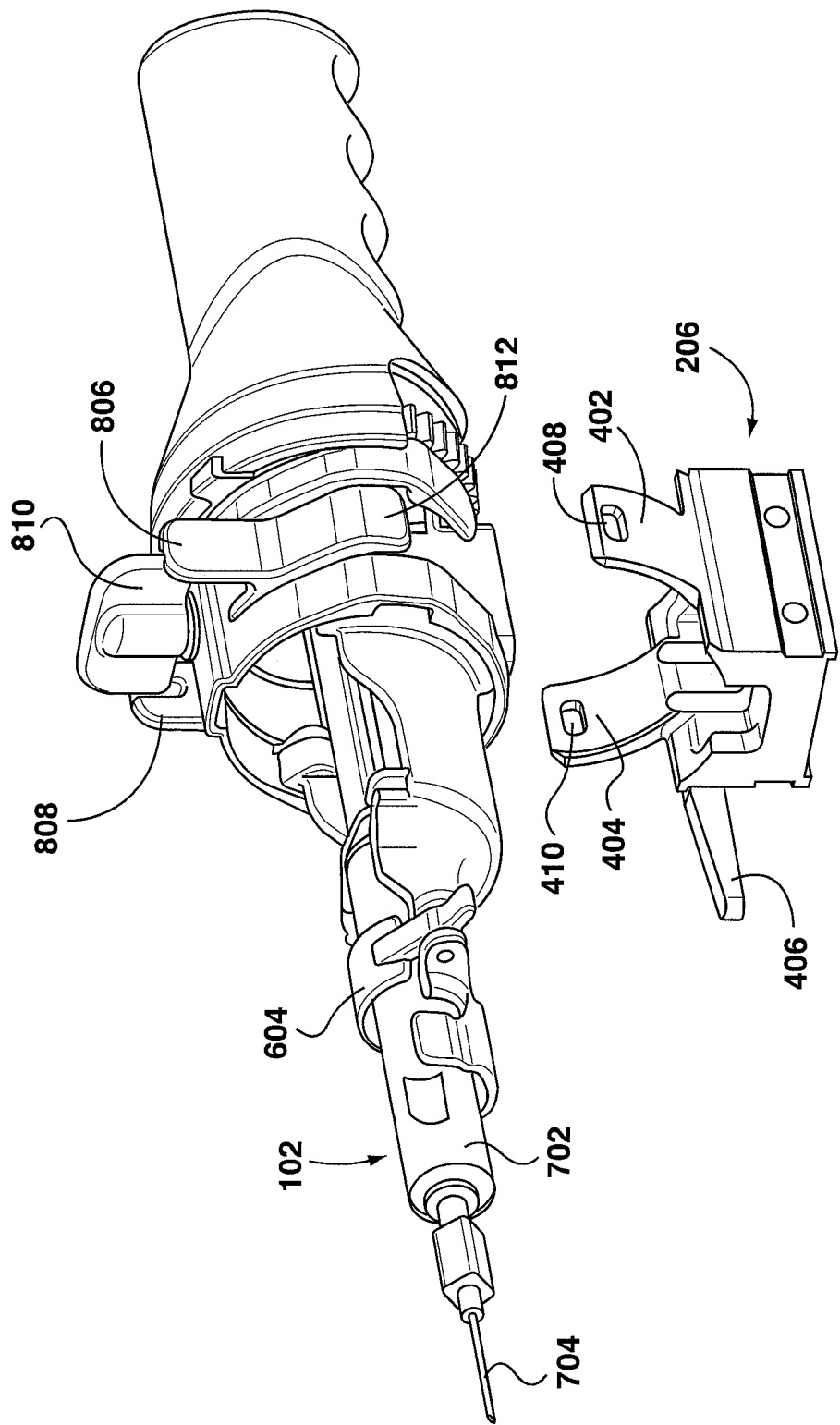
FIG. 16 is a perspective view showing a tool mount adaptor securing a medical instrument and showing the relationship of a tool mount adaptor with an end effector interface according to some embodiments of the invention.
Figure 17:
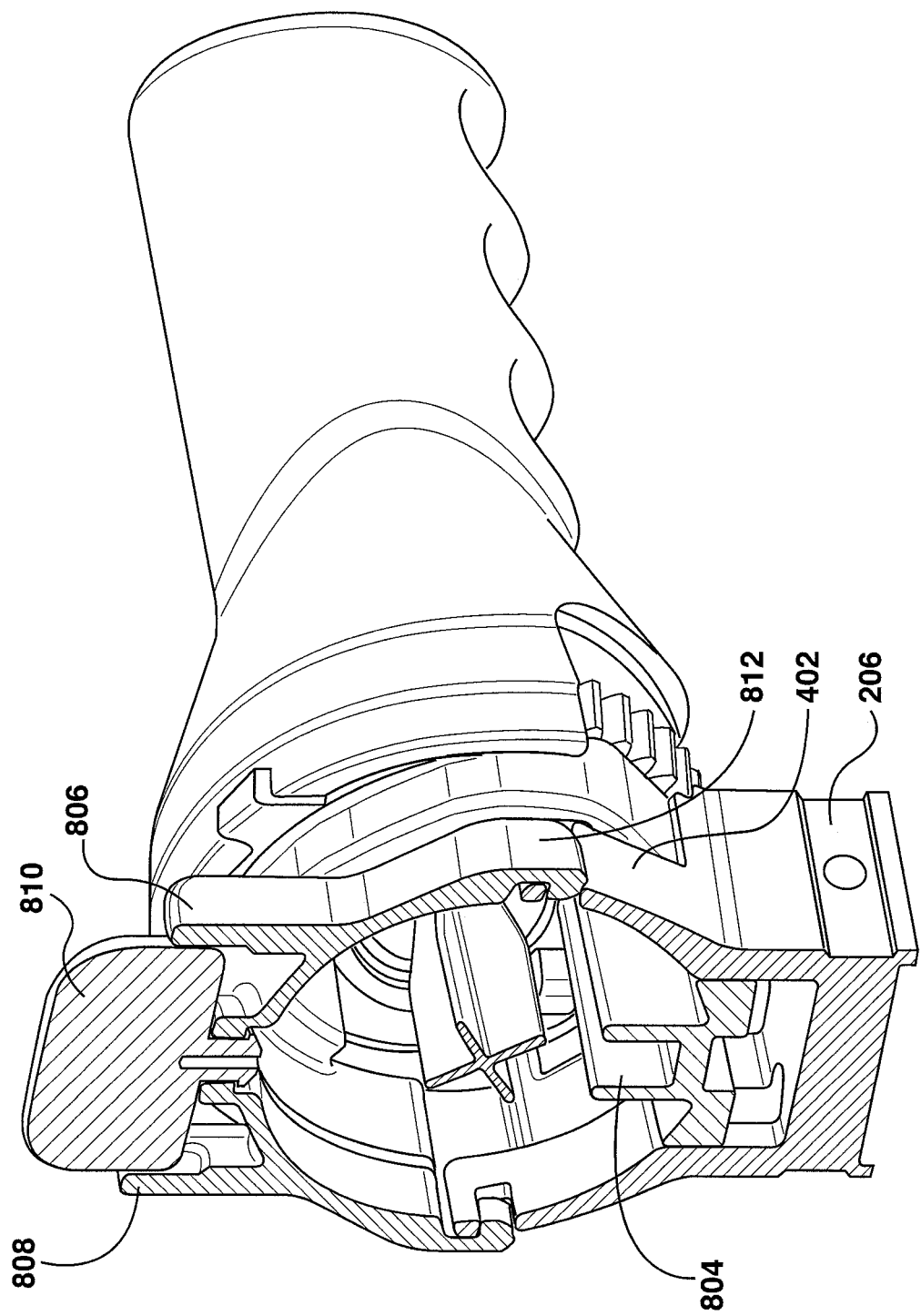
FIG. 17 is a perspective view showing a tool mount adaptor secured to an end effector interface according to some embodiments of the invention.

The medical instrument or tool can be any instrument generally used for insertion into a specimen, such as a patient, and can include, but is not limited to, trocars, syringes, needles, fibreoptic sensors, interstitial imaging devices, biopsy tools, probes, or ablative tools. Referring to FIG. 16, medical instrument 102 can include main body 702 and elongate member 704 such as a needle which extends from main body 702. In example embodiments, elongate member 704 is formed from MR compatible materials such as carbon fibre, ceramic, or titanium. Another example of the medical instrument is a biopsy tool, such as a vacuum assisted biopsy device, as would be understood in the art. Elongate member 704 can also include an ablative tool such as Radio Frequency (RF) ablation, focused ultrasound, cryotherapy, laser and other ablative technologies that are administered within the cancerous region causing cell destruction with minimal damage to surrounding tissues. In some example embodiments, the medical instrument can also include a detector such as a probe, ultrasound probe, or fiber optic probe. The detector can also include an MRI coil to provide higher resolution in situ imaging. In yet further example embodiments, the medical instrument can be integrated with the end effector interface and the tool mount adaptor to result in a dedicated-purpose insertion device. In yet further example embodiments, the medical instrument can include an end effector or end effectors.

In some embodiments, medical instrument 102 can be mounted to medical insertion device 100 generally laterally to axis 127. Collar 802, with attached medical instrument 102, can couple to mounting tray 600 laterally. Collar 802, having medical instrument 102 secured therein, can be attached to end effector interface 206 through a securing mechanism as described herein. By mounting medical instrument 102 lateral to axis 127 rather than along axis 127, the chances of accidentally poking or piercing a patient can be reduced. The skilled person will recognize that the mounting of a medical instrument 102 can also be performed generally parallel to axis 127, or at any angle between parallel and perpendicular to this axis as afforded by the specific embodiment of the device.

Medical instruments interfaced with the medical insertion device can be inserted into a patient for various purposes, such as for therapeutic or diagnostic purposes. Medical instruments can include biopsy tools for taking tissue samples, such as vacuum assisted biopsy (VAB) tools or devices available from ATEC™, or other manufacturers of similar VAB tools or devices; ablative tools for removing unwanted tissue, such as radio frequency (RF) ablation, focused ultrasound, cryotherapy, laser and other ablative technologies; detectors for determining characteristics of tissue such as probes, ultrasound probes, or fibre optic probes, the detectors may include an MRI coil to provide higher resolution in situ imaging; or end effectors for general manipulation during an operation. Medical instruments may be inserted into a patient to an insertion depth in accordance with a particular procedure. The insertion depth may be predetermined by an operator, or can be determined during insertion by reference to sensors, such as force feedback sensors for determining the type of tissue the medical instrument has been inserted into, or imaging technologies, such as, but not limited to, cameras, x-ray systems, ultrasound systems, positron emission tomography (PET) systems, positron emission mammography (PEM) systems, CT laser mammography systems, and molecular biological imagers.

Figure 18:
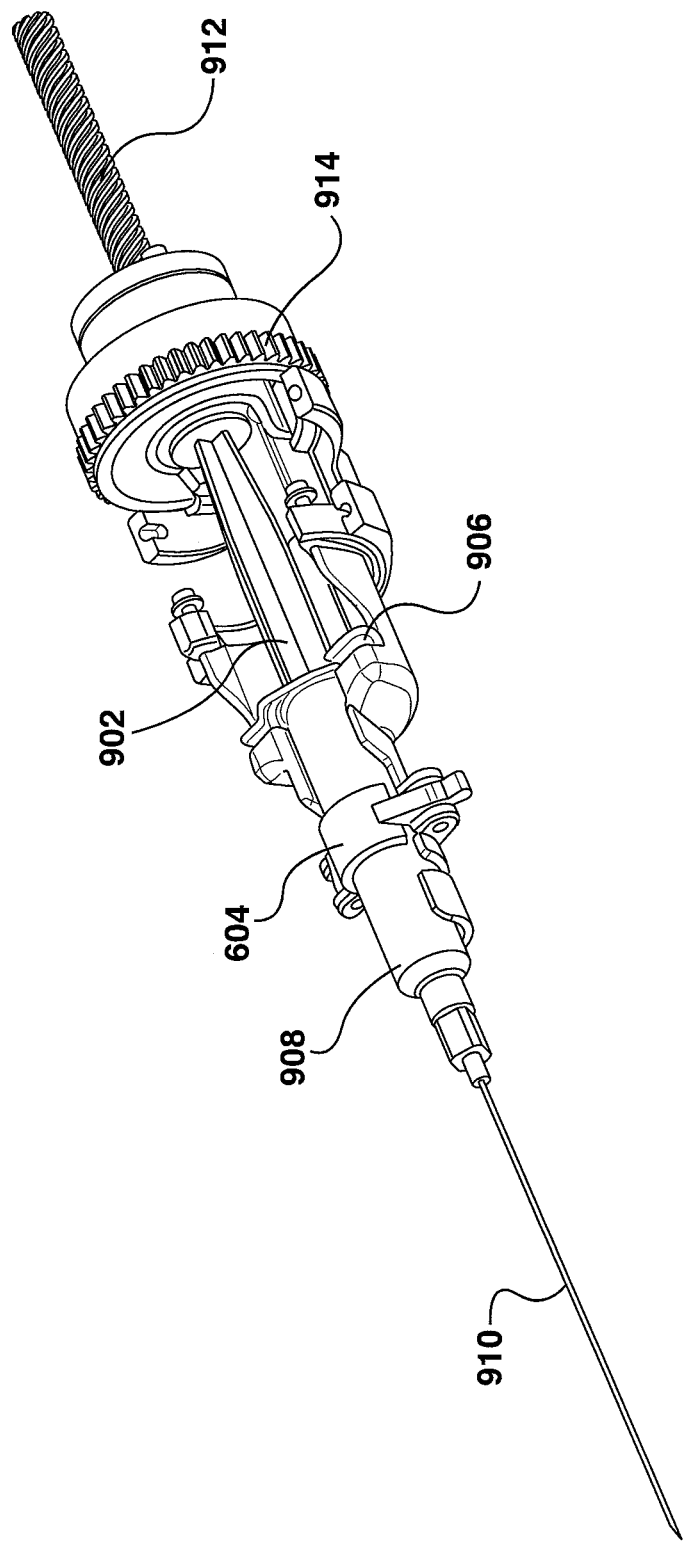
FIGS. 18 and 19 are perspective views depicting an anesthesia tool attached to a collar of a tool mount adaptor according to various embodiments of the present invention.
Figure 19:
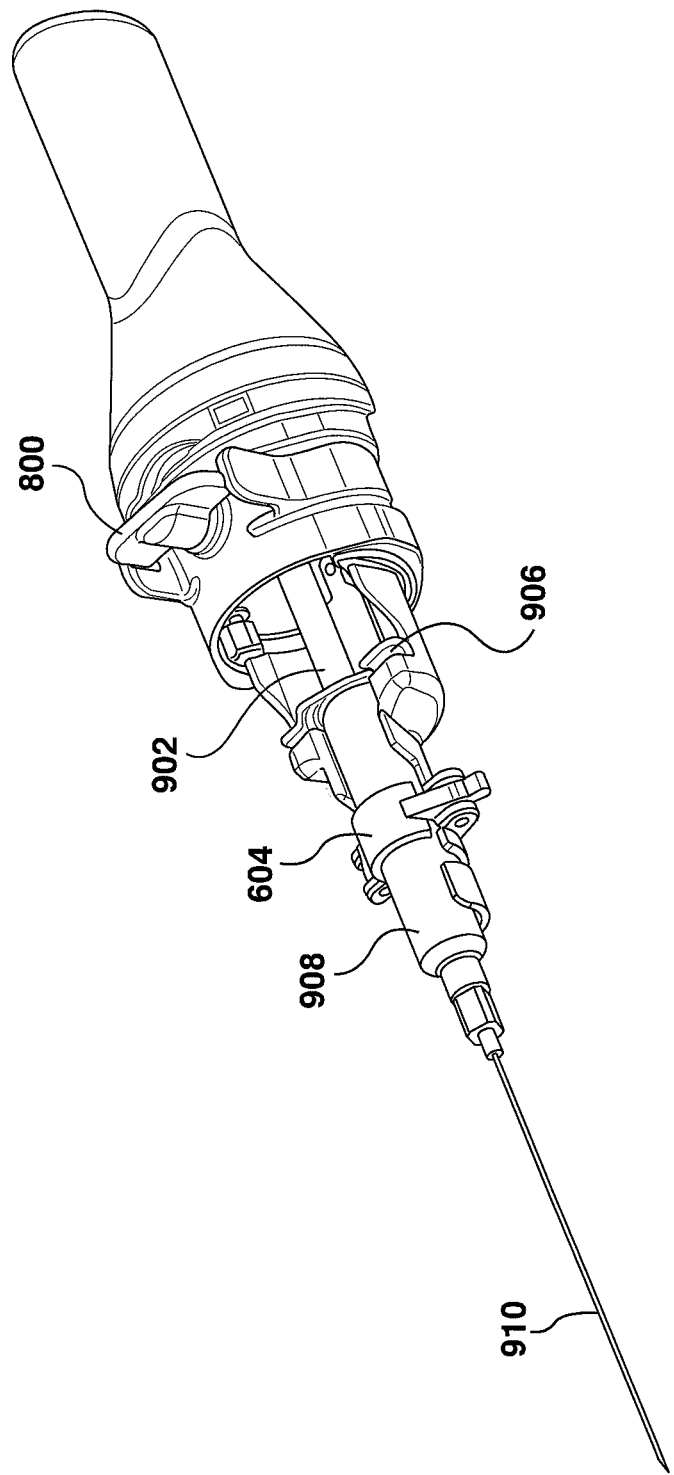
Figure 20:
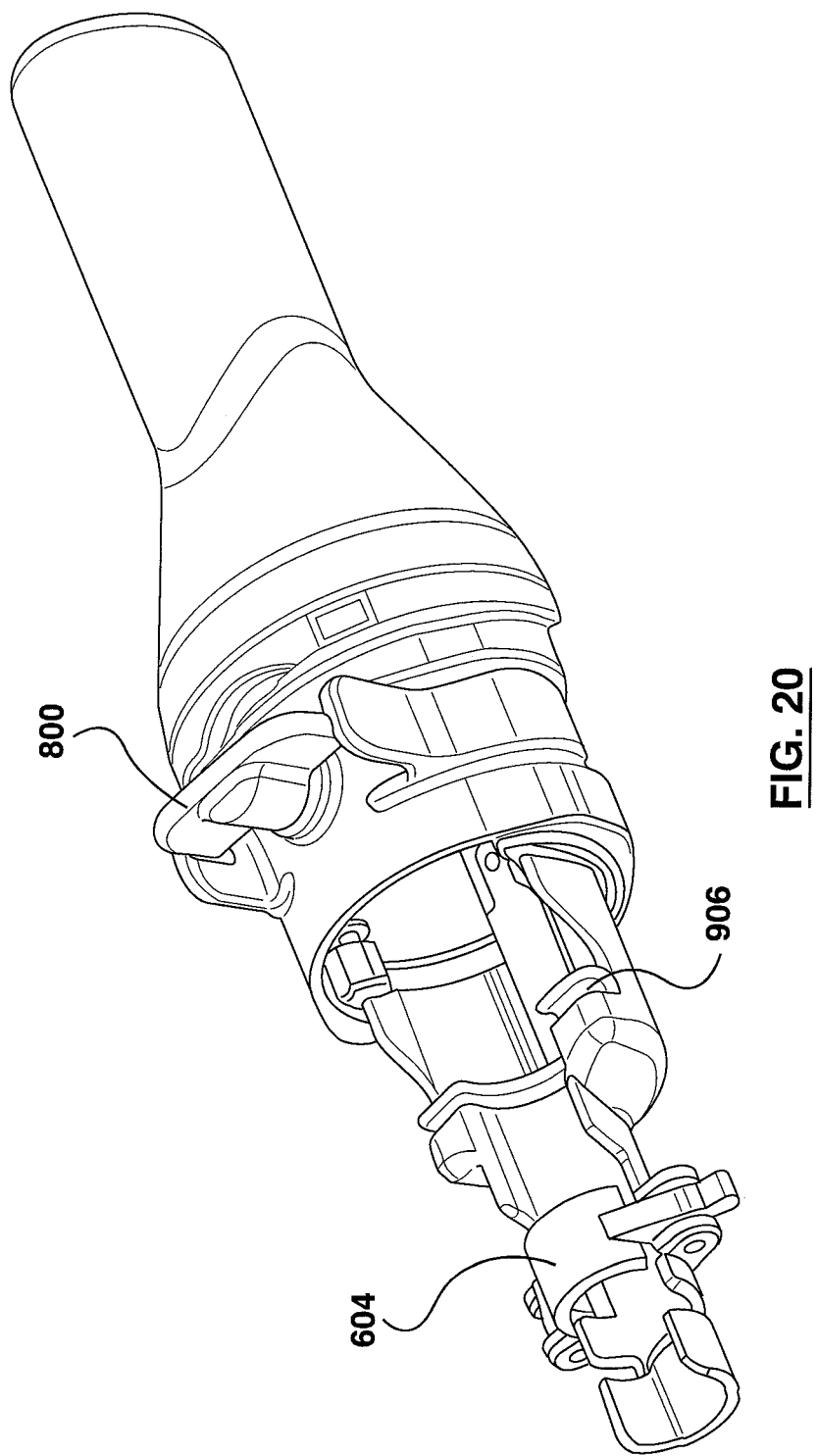
FIGS. 20 and 21 are perspective views showing the tool mount adaptor shown in FIGS. 18 and 19 without the anesthesia tool.
Figure 21:
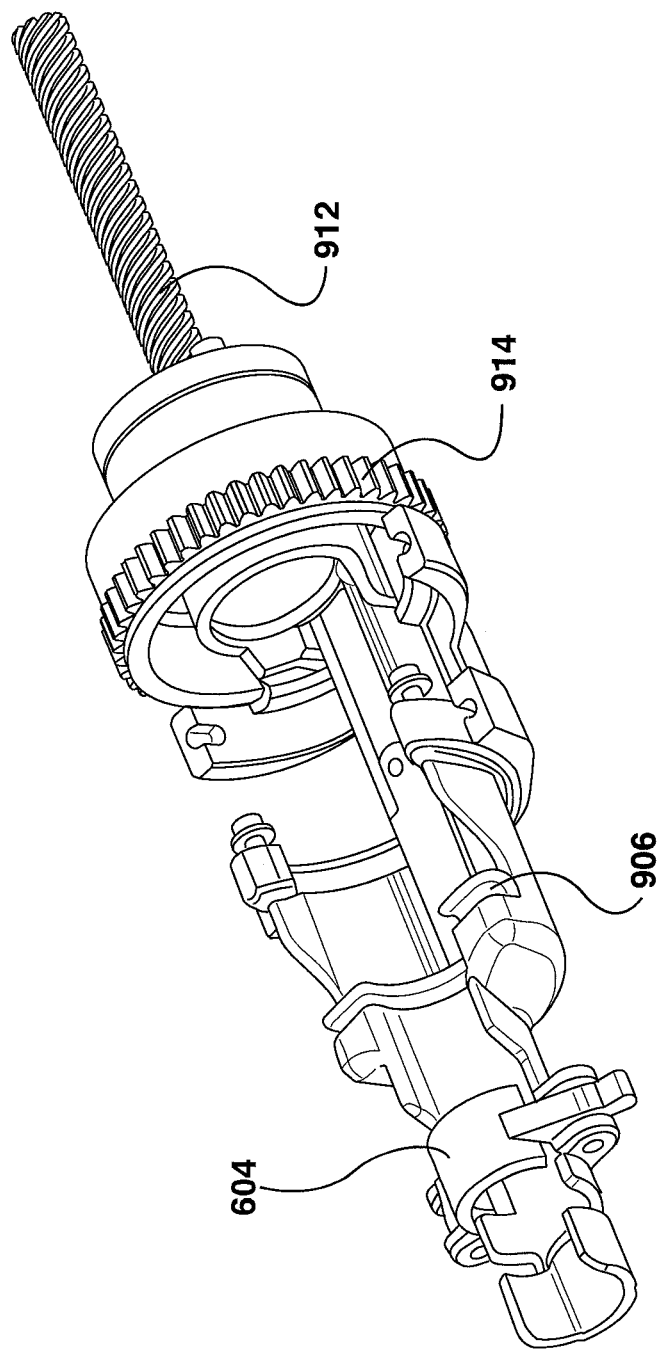
Figure 22:
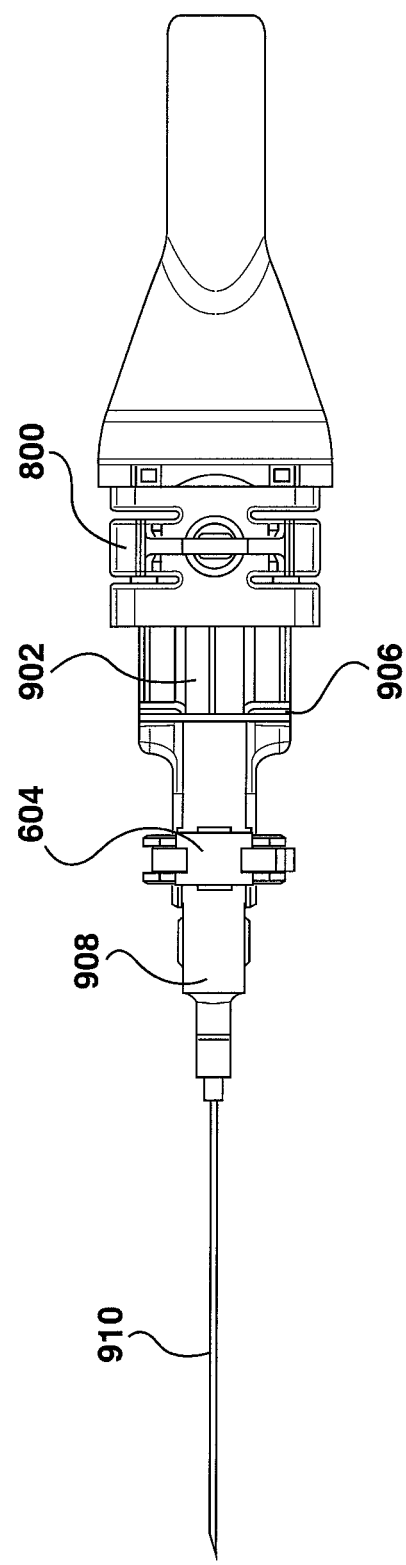
FIG. 22 is a planar view of an anesthesia tool attached to the collar of the tool mount adaptor shown in FIG. 19.

FIGS. 16, 17, 18, 19, 20, 21 and 22 show other embodiments of the tool mount adaptor, which can be mounted to end effector interface 206, described above, or a similar adaptor of a robotic device that is designed to position interventional tools at a specific location. In some embodiments, the medical instrument can be an anesthesia tool, for example, a syringe. In FIGS. 18, 19 and 22, tool mount adaptor 800 can contain a latch 604 to hold an off-the-shelf syringe 908. Tool mount adaptor 800 can employ physical (i.e., mechanical) mechanisms to ensure that the off-the-shelf syringe 908 is secured to tool mount adaptor 800. This includes a means of keeping the off-the-shelf syringe 908 in place laterally (e.g., a "tight fit" mould or a secondary security latch that fits around the syringe) and along the length of the syringe (e.g., a latch 604, or a syringe slot 906 for the flange at the base of the off-the-shelf syringe 908, normally used to put two fingers against and provide the required resistance against the push of the plunger with your thumb).

In some embodiments, tool mount adaptor 800 can be constructed so that an off-the-shelf needle 910 mounted to the off-the-shelf syringe 908 will be aligned with a known trajectory. When the tool mount adaptor 800 is translated in a fashion that is co-linear with the centerline of the off-the-shelf syringe 908 (e.g., by a robotic or mechanical manipulator system such as medical insertion device 100 along axis 127), the off-the-shelf needle 910 can travel in a straight line along this trajectory. In an embodiment, tool mount adaptor 800 can also mount the off-the-shelf syringe 908 such that if (a) the syringe dimensions are known and (b) the needle length is known, then the location of the tip of the off-the-shelf needle 910 can be calculated to a high degree of accuracy. Consequently, the trajectory of the tip will be along the same path as the main body of the off-the-shelf needle 910, and, therefore, (a) the trajectory of the tip and (b) the final placement of the full length of the off-the-shelf needle 910 can be calculated as well.

Tool mount adaptor 800 can also be adapted to depress or retract the syringe plunger 902 of the off-the-shelf syringe 908. In some embodiments, tool mount adaptor 800 comprises a linear screw 912 that can interface with a drive gear 914. The drive gear 914 interfaces with another set of gears on a robotic manipulator, for example, medical insertion device 100 such that a motor (that is part of the robotic manipulator) can cause the syringe plunger 902 to be depressed or retracted. If the linear screw 912 does not have a means to attach to the syringe plunger 902, then the robotic device will only be able to depress the syringe plunger 902 (i.e., will only be able to expel the injectate from the syringe). If, however, a means is provided for the linear screw 912 to couple with the syringe plunger 902 (e.g., a snap-on clip that secures them to each other), then the direction of rotation of the drive gear 914, as initiated by the robotic device, will determine whether the syringe plunger 902 is depressed (e.g., for deploying anesthetic) or retracted (e.g., for aspirating fluid from a cyst).

The mechanism by which the syringe plunger 902 is depressed or retracted (e.g., the "linear screw") can be fully decoupled from physical motion (translation or rotation) of the tool mount adaptor itself. In some embodiments of the medical insertion device and end effector interface, an independent rotating gear actuates the drive gear 914 on the tool mount adaptor 800. This allows the off-the-shelf needle 910 to be positioned at a defined spatial location, without depressing or retracting the syringe plunger 902. It also allows the options of (a) leaving the off-the-shelf needle 910 at a known location while depressing (e.g. to inject) or retracting (e.g., to aspirate) the syringe plunger 902; (b) moving the off-the-shelf needle 910 while depressing or retracting the syringe plunger 902 (e.g., to inject anesthetic along a path inside tissue); or (c) any combination of the two, where the off-the-shelf needle 910 traverses a defined path with or without the syringe plunger 902 being depressed or retracted.

Figure 23:
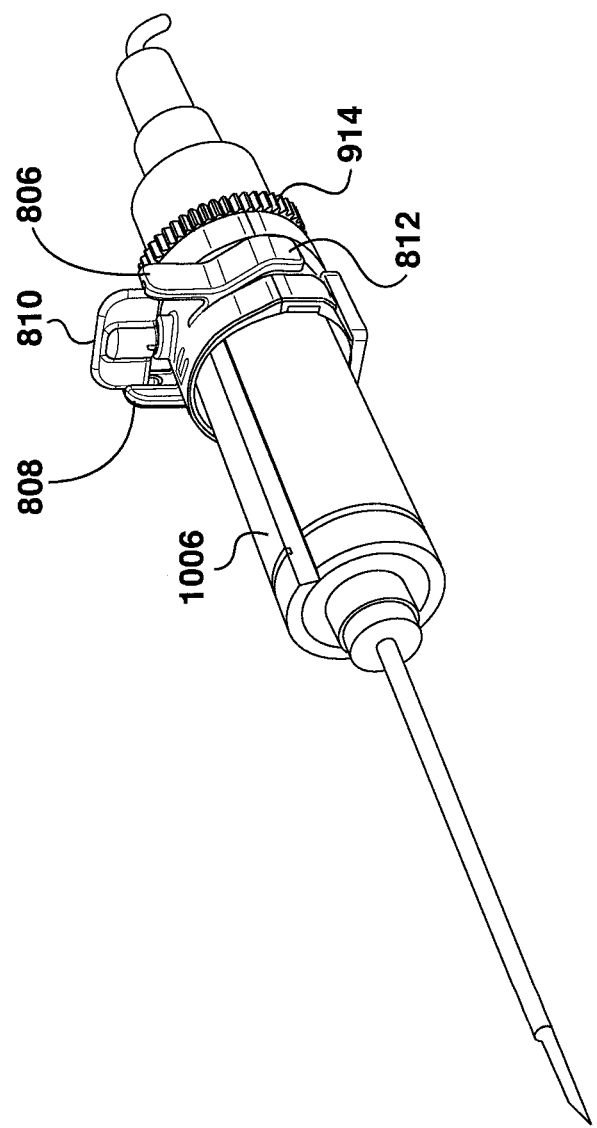
FIG. 23 is a perspective view depicting a vacuum assisted biopsy (VAB) tool attached to a collar of the tool mount adaptor according to an embodiment of the present invention.
Figure 24:
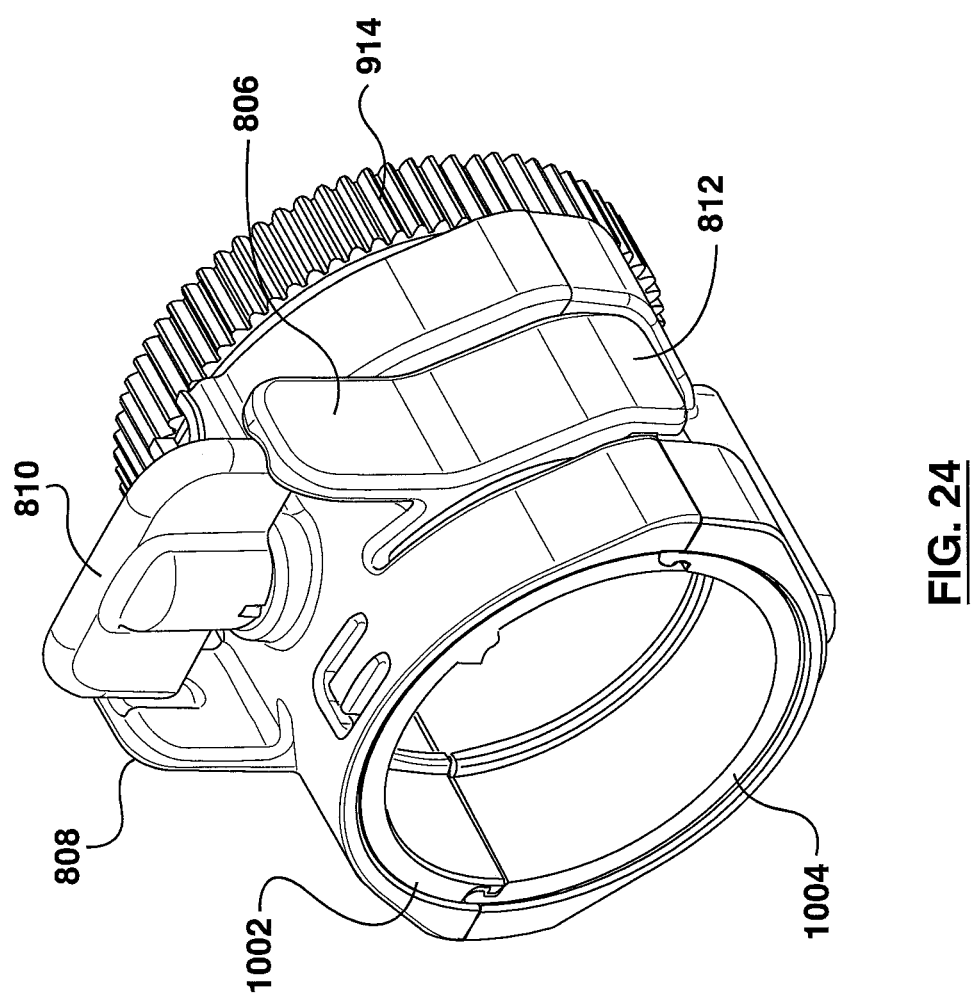
FIG. 24 is a perspective view depicting the tool mount adaptor shown in FIG. 23.

Referring to FIGS. 23, 24 and 25, another embodiment of the tool mount adaptor will be described, which can mount to the end effector interface, described above, or a similar adaptor of a robotic device that is designed to position interventional tools at a specific location. In some embodiments, the medical instrument can be a vacuum assisted biopsy tool. In some embodiments, tool mount adaptor 800 can contain "tight fit" moulds 1002 and 1004 to secure an off-the-shelf biopsy tool to a robotic end effector. These "tight fit" moulds 1002 and 1004 may contain internal grooves and shoulders that interface with corresponding features on a medical instrument to ensure a "tight fit" assembly. Alternatively, this interface may be secured by screws, glue, or any other means known in the art.

Tool mount adaptor 800 can be constructed so that an off-the-shelf biopsy tool 1006 will be aligned with a known trajectory. When the tool mount adaptor 800 is translated in a fashion that is co-linear with the centerline of the off-the-shelf biopsy tool 1006 (e.g., by a robotic or mechanical manipulator system such as medical insertion device 100 along axis 127), the off-the-shelf biopsy tool 1006 can travel in a straight line along this trajectory. Tool mount adaptor 800 can also mount the off-the-shelf biopsy tool 1006 such that if the length of the biopsy tool needle is known, then the location of the tip of the off-the-shelf biopsy tool 1006 can be calculated to a high degree of accuracy. Consequently, the trajectory of the biopsy tool tip will be along the same path as the main body of the off-the-shelf biopsy tool 1006, and, therefore, (a) the trajectory of the tip and (b) the final placement of the full length of the off-the-shelf biopsy tool 1006 can be calculated as well.

Tool mount adaptor 800 can also be adapted to roll the off-the-shelf biopsy tool 1006. This roll functionality may be used to rotate the aperture of the biopsy tool around the axis of the biopsy tool, which could enable 360° of sampling. In an embodiment, tool mount adaptor 800 comprises a drive gear integrated into "tight fit" moulds 1002 and 1004. The drive gear on "tight fit" moulds 1002 and 1004 interfaces with another set of gears on a robotic manipulator, for example, medical insertion device 100 such that a motor (that is part of the robotic manipulator) can cause the off-the-shelf biopsy tool 1006 to be rolled. The direction of rotation of the drive gear is controlled by the robotic device, and will determine whether the off-the-shelf biopsy tool 1006 is rotated clockwise or counterclockwise.

The mechanism by which the off-the-shelf biopsy tool 1006 is rotated (i.e., the drive gear) can be fully decoupled from physical motion (translational) of the tool mount adaptor 800 itself. In some embodiments of the medical insertion device 100 and end effector interface 206, an independent rotating gear actuates the drive gear on "tight fit" moulds 1002 and 1004. This allows the off-the-shelf biopsy tool 1006 to be positioned at a defined spatial location without any rotational motion. It also allows the options of leaving the off-the-shelf biopsy tool 1006 at a known location while rotating the aperature window.

In some embodiments, there is provided a method for facilitating insertion of a medical instrument in a patient using a medical insertion device, the medical insertion device comprising: (a) a frame; and (b) a carriage assembly connected to the frame comprising: (i) a mounting arm comprising an insertion track; (ii) an insertion carriage adapted to move along the insertion track; and (iii) a tool mount adaptor connected to the insertion carriage, the tool mount adaptor comprising a collar for holding a medical instrument and a medical instrument held in the collar, wherein the tool mount adaptor is releasably attachable to the insertion carriage, the method comprising: moving the insertion carriage along the insertion track in an insertion direction toward the patient. In other embodiments of the method, the mounting arm of the carriage assembly further comprises a cannula track parallel to the insertion track; and the carriage assembly further comprises a cannula carriage, wherein the cannula carriage comprises a demobilizer, a cannula holder mount for receiving a cannula, and a cannula held in the cannula holder mount, wherein the cannula carriage is adapted to move along the cannula track, and the demobilizer in a demobilization mode is adapted to restrict movement of the cannula carriage along the cannula track and in a mobilization mode allows movement of the cannula carriage along the cannula track. In operation, insertion carriage 124 can move along insertion track 122 along axis 127 toward a patient. When protrusion 406 abuts cannula holder mount 204, movement lock 208 is engaged as described above to unlock cannula holder mount 204 from cannula track 210, thereby allowing insertion carriage 124 and cannula holder mount 204 to continue along axis 127, and ultimately insert medical instrument 102 and/or cannula 103 into the patient. For example, medical instrument 102 can function as an introducer for an initial insertion into the patient. When the desired insertion depth on the patient is reached, end effector interface 206 and medical instrument 102 can retract, causing movement lock 208 to once again lock to cannula track 210, causing cannula 103 to remain in place in the patient. Medical instrument 102 attached to retracted tool mount adaptor 800 can then be replaced with alternative instruments and inserted into the patient without additional invasive insertions.

Medical instrument 102 and cannula 103 can operate in conjunction with each other. For example, medical instrument 102 can be a trocar, which can act as a cutter. According to some embodiments, cannula 103, sometimes called an introducer, can be introduced to the desired site within a patient after a trocar is used to create the initial puncture through the patient's skin. Once cannula 103 is placed at the desired site by way of the trocar, the trocar can removed and the cannula can be left in place for other tools to traverse the same path. Cannula 103 can then provide a path through which multiple interventional tools will pass. This avoids extra punctures through the skin and additional trajectories for different tools through the tissue. Once retracted, the trocar can then be exchanged with a different medical instrument, such as, but not limited to, a medical instrument useful for endoscopy, biopsy, anesthesia, ablation, imaging, spectroscopy, aspiration, and the like. This can allow for a variety of procedures to be performed while minimizing the number of invasive insertions into the patient.

Generally, the medical insertion device can be used in conjunction with an imaging system (not shown here), such as a magnetic resonance imaging (MRI) system, when the imaging system is in use. Other imaging systems with which the medical insertion device can be used include, but are not limited to, cameras, x-ray systems, ultrasound systems, positron emission tomography (PET) systems, single photon emission compute tomography (SPECT) systems, optical coherence tomography (OCT) systems, optical imaging and/or spectroscopy systems, thermal imaging systems, positron emission mammography (PEM) systems, CT laser mammography systems, and molecular biological imagers.

Figure 26A:
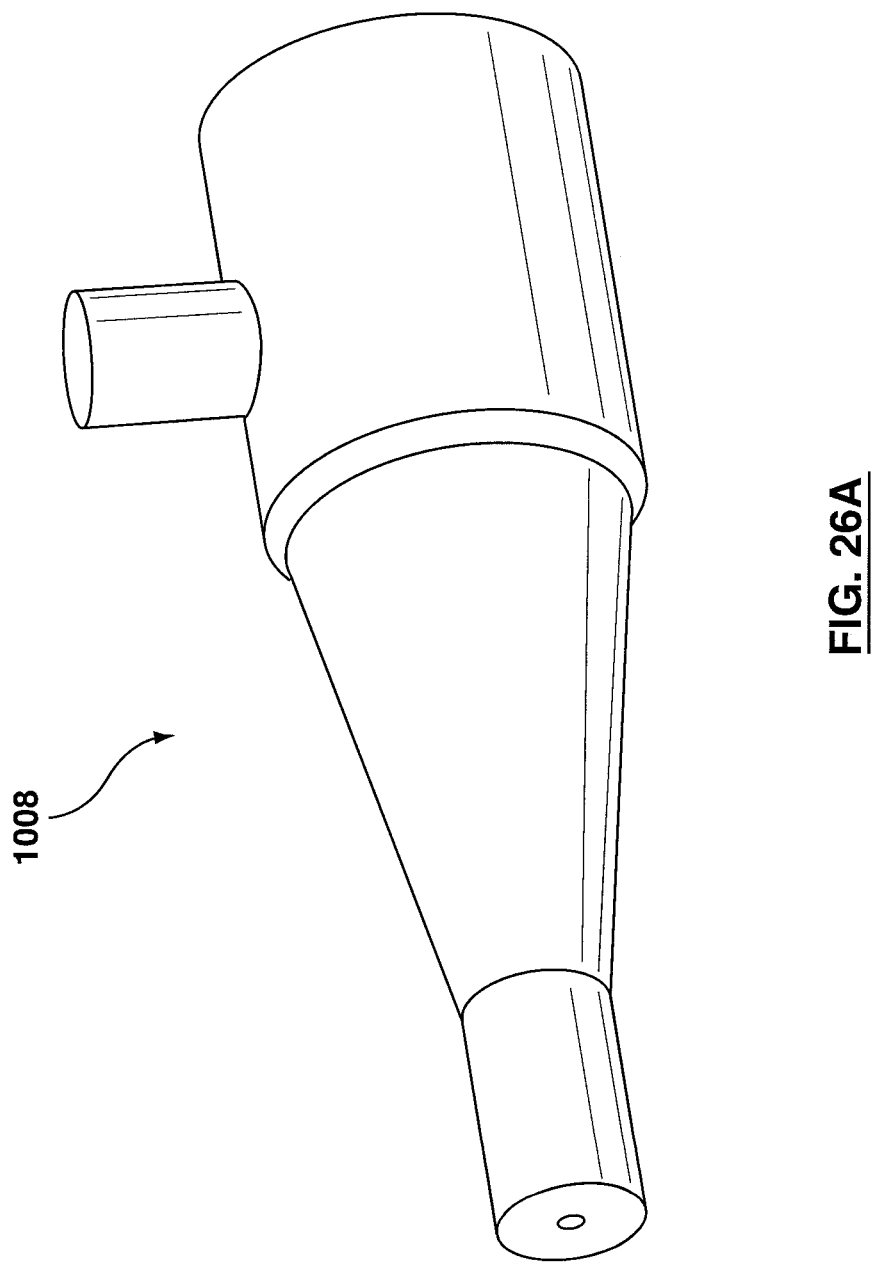
FIGS. 26A and 26B are perspective views showing a needle guide according to embodiments of the invention.
Figure 26B:
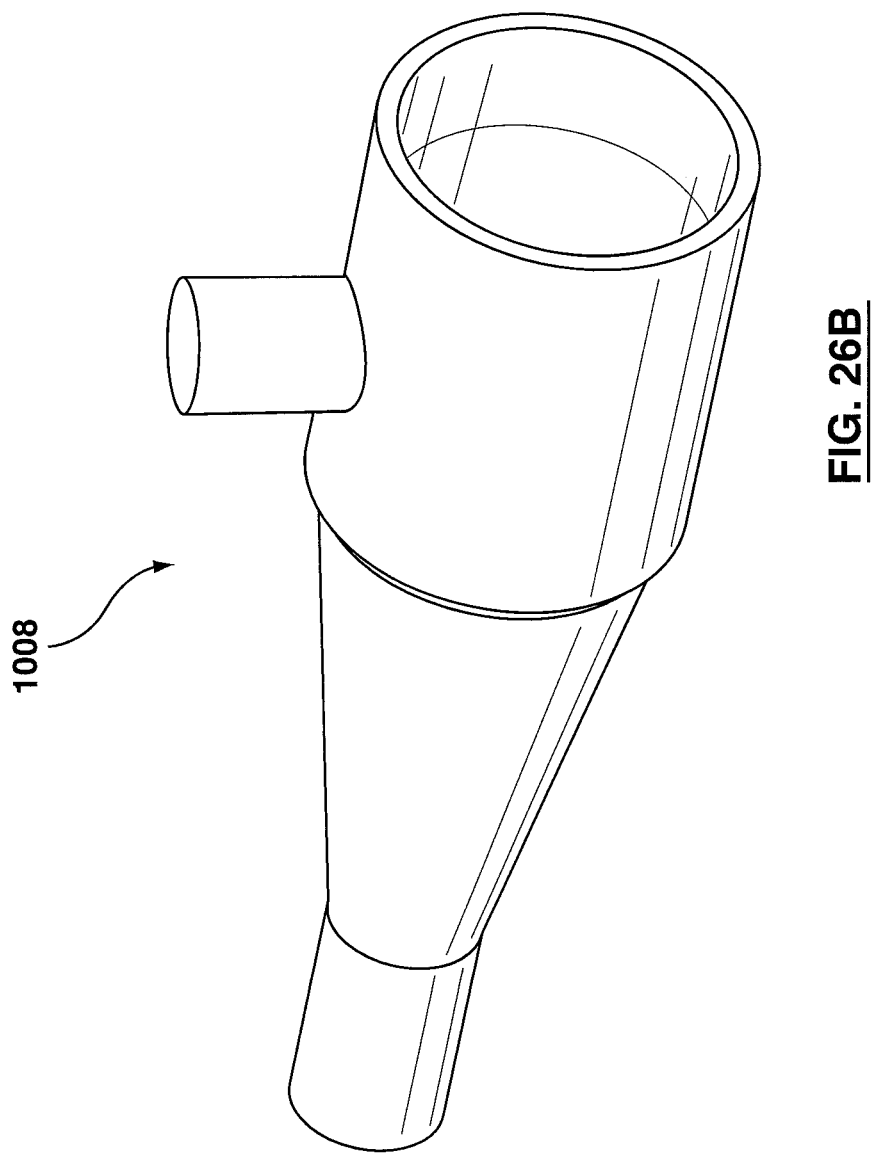
Figure 27:
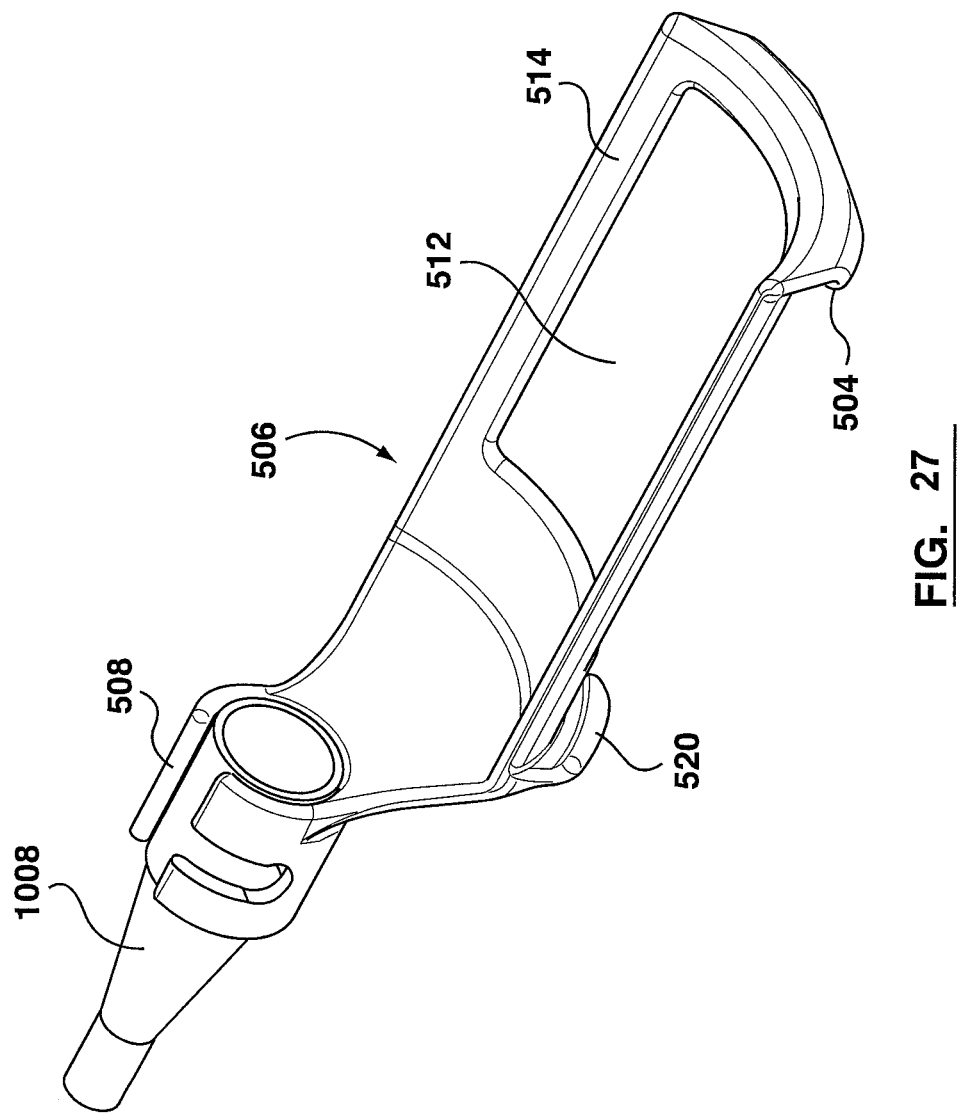
FIG. 27 is a perspective view showing a needle guide coupled to a cannula holder according to various embodiments of the invention.

Referring to FIGS. 26A, 26B and 27, another embodiment of the invention will be described. In some embodiments, a needle guide 1008 is also provided. The needle guide 1008 is designed to mount to the cannula holder mount 204 on the cannula track 210 of the interface and move independently of the tool mount adaptor 800. Alternatively, one skilled in the art can appreciate that the needle guide 1008 could be constructed to interface with the cannula holder 506 instead of (and in the same manner as) the cannula 103 locks into the cannula holder securing mechanism 508. In some embodiments, the needle guide 1008 may be placed near the skin surface to guide the off-the-shelf needle 910 to a specific entry point. A hole in the needle guide 1008 is designed to be in the correct location such that the off-the-shelf needle 910 will pass through it while traversing the trajectory that has already been defined according to the design of the tool mount adaptor 800. When the medical insertion device 100 pushes the tool mount adaptor 800 forward (via the end effector interface 206), the off-the-shelf needle 910 consequently passes through the needle guide 1008 before going into the underlying tissue. This needle guide 1008 (a) provides a visual cue as to where the off-the-shelf needle 910 will enter the skin and (b) provides mechanical support for maintaining a straight needle path as it enters the tissue.

In some embodiments, suitable materials for the various described assemblies, subsystems and devices can be, for example, ceramics, thermoplastics, thermoset plastics, carbon fibre, composites, nanoparticle composites, aluminum, titanium, or stainless steel. In other embodiments, when the various assemblies, subsystems and devices described herein are intended to be used with magnetic resonance technologies, suitable materials for the assemblies, subsystems and devices can be, for example, magnetic resonance compatible materials. In some embodiments, MR compatible materials can be, for example, ceramics, thermoplastics or thermoset plastics. In other embodiments, suitable materials can be, for example, carbon fibre, composites, nanoparticle composites, aluminum, titanium, or stainless steel. In some embodiments, MR compatible motors can be, for example, piezoelectric motors, pneumatic, vacuum-actuated or hydraulic drivers. If described devices are not intended to be MRI compatible, other materials, such as metal components or standard inductive electrical motors, can be suitable. The various described assemblies, subsystems and devices can be manufactured using additive manufacturing methods. In some embodiments, the tool mount adaptor can be manufactured by using, for example, 3D printing. In some embodiments, for example, 3D printing can build an object or device from a series of layers, each layer being printed directly on top of a previous layer. In further embodiments, for example, a 3D printing model for the object or device can be created with a computer aided design package or via a 3D scanner. According to other embodiments, to manufacture the object or device, the 3D printer can read the design from a 3D printable file and can lay down successive layers of the raw material (for example, liquid, powder, paper or sheet material) to build the model from a series of cross sections. These layers, which may correspond to the virtual cross sections from the CAD model, may be joined or automatically fused to create the final shape of the object or device. In some embodiments, for example, the 3D printing can use lasers or electron beams to join or fuse the layers.

Generally speaking, the invention provides for the operable co-operation of a tool mount adaptor for securing a medical instrument and a cannula holder for securing a cannula. The tool mount adaptor can be constructed so that off-the-shelf tools or custom tools will be aligned with a known trajectory. This trajectory may be straight or angular as controlled by a robotic manipulator, for example, medical insertion device 100. Tool mount adaptors can also secure tools such that if the length of the tool is known, then the location of the tip of the tool can be calculated to a high degree of accuracy. Consequently, the trajectory of the biopsy tool tip will be along the same path as the main body of the tool, and, therefore, (a) the trajectory of the tip and/or (b) the final placement of the full length of the off-the-shelf biopsy tool can be calculated.

The tool mount adaptor can be coupled to a medical insertion device comprising a mounting arm, an insertion track mounted on the mounting arm, an insertion carriage adapted to be slideably moveable along the instrument track, and a cannula track mounted on the mounting arm, generally parallel to the insertion track. The tool mount adaptor can be coupled to the insertion carriage and the cannula holder can be coupled to the cannula track such that the medical instrument and the cannula are slideably moveable along the same axis. At least a portion of the body of the medical instrument can be accommodated by the hollow body of the cannula. When an operator causes the insertion carriage to move along the insertion track in the insertion direction, for example to insert the medical instrument into a patient, the tool mount adaptor can disengage the cannula holder and can allow both the tool mount adaptor and the cannula holder to proceed in the insertion direction until the medical instrument and the cannula reach an insertion depth within a patient. The tool mount adaptor can then be retracted, leaving the cannula holder to remain in place. This allows an operator to mount a different medical instrument to the medical insertion device to perform additional tasks while not requiring additional invasive insertions into a patient.

Variations may be made to the medical insertion device in example embodiments. For example, in some example embodiments, an insertion mechanism may be used to move the entire linear slide assembly 106 in the insertion direction 127 to provide the insertion step (rather than from the insertion track 122). In some additional embodiments, some medical instruments 102 may include their own insertion or injection mechanism, which may be automated or manually controllable by a mechanism for insertion.

Specific examples of the assembly and components have been described for illustrative purposes. These are only examples. The technology provided can be applied to systems other than the given examples. Those of skill in the art will recognize certain modifications, permutations, additions and sub-combinations thereof. It is therefore intended that the following appended claims and claims hereafter introduced are interpreted to include all such modifications, permutations, additions and sub-combinations.

We claim:

1. A method for facilitating insertion of a medical instrument in a patient using a medical insertion device, the medical insertion device comprising:
   (a) a frame; and
   (b) a carriage assembly connected to the frame comprising:
      (i) an insertion track;
      (ii) a cannula track parallel to the insertion track;
      (iii) an insertion carriage adapted to move along the insertion track;
      (iv) a tool mount adaptor connected to the insertion carriage for receiving a medical instrument; and
      (v) a cannula carriage adapted to move along the cannula track; the cannula carriage comprising:
      a cannula holder mount for receiving a cannula,
   the method comprising:
   (A) securing a medical instrument in the tool mount adaptor;
   (B) securing a cannula to the cannula holder mount and moving the insertion carriage along the insertion track in the insertion direction wherein the insertion carriage engages the cannula carriage to allow movement of the cannula carriage along the cannula track in the insertion direction;
   (C) actuating at least one functionality of the medical instrument held within the tool mount adaptor;
   (D) moving the insertion carriage along the insertion track in a direction opposite to the insertion direction to retract the medical instrument from the patient;
   wherein movement of the insertion carriage along the insertion track in a direction opposite to the insertion direction engages the cannula carriage to restrict movement of the cannula carriage along the cannula track.

2. The method of claim 1, further comprising removing the medical instrument from the tool mount adaptor.

3. The method of claim 1 comprising removing the medical instrument from the tool mount adaptor and securing a second medical instrument in the tool mount adaptor and moving the insertion carriage along the insertion track in an insertion direction to insert the second medical instrument into the patient.

4. The method of claim 3, further comprising moving the cannula carriage along the cannula track in a direction opposite to the insertion direction to retract the cannula from the patient.

5. The method of claim 4, further comprising removing the cannula from the cannula holder mount.

6. The method of claim 4, wherein the cannula carriage comprises a demobilizer, wherein the demobilizer in a demobilization mode is adapted to restrict movement of the cannula carriage along the cannula track and in a mobilization mode allows movement of the cannula carriage along the cannula track.

7. The method of claim 4 wherein the functionality of the second medical instrument is a biopsy tool functionality.

8. The method of claim 4, wherein the tool mount adaptor is releasably attachable to the insertion carriage.

9. The method of claim 1, wherein the cannula carriage comprises a demobilizer, wherein the demobilizer in a demobilization mode is adapted to restrict movement of the cannula carriage along the cannula track and in a mobilization mode allows movement of the cannula carriage along the cannula track.

10. The method of claim 1 wherein the functionality of the medical instrument is at least one of a trocar functionality, a syringe functionality and a biopsy tool functionality.

11. The method of claim 1, wherein the tool mount adaptor comprises a collar.

12. The method of claim 11, wherein the method comprises securing an anesthesia tool in the collar, moving the insertion carriage along the insertion track in an insertion direction to insert the anesthesia tool into the patient, moving the insertion carriage along the insertion track in a direction opposite to the insertion direction to retract the anesthesia tool from the patient and removing the anesthesia tool from the collar; securing a trocar in the collar and moving the insertion carriage along the insertion track in an insertion direction to insert the trocar into a single access point of a patient; securing a cannula to the cannula holder mount and moving the cannula carriage along the cannula track in the insertion direction to insert the cannula into the single access point of the patient; moving the insertion carriage along the insertion track in a direction opposite to the insertion direction to retract the trocar from the patient and removing the trocar from the collar; securing a biopsy tool to the collar and moving the insertion carriage along the insertion track in the insertion direction to insert the biopsy tool into the single access point of the patient and through a hollow body of the cannula; moving the insertion carriage along the insertion track in a direction opposite to the insertion direction to retract the biopsy tool from the patient and removing the biopsy tool from the collar; and moving the cannula carriage along the cannula track in a direction opposite to the insertion direction to retract the cannula from the patient and removing the cannula from the cannula holder mount.

13. The method of claim 1, wherein the tool mount adaptor is releasably attachable to the insertion carriage.

* * * * *